United States Patent
Riber et al.

(10) Patent No.: US 10,442,847 B2
(45) Date of Patent: Oct. 15, 2019

(54) GLUCAGON ANALOGUES

(71) Applicant: Zealand Pharma A/S, Glostrup (DK)

(72) Inventors: Ditte Riber, Brønshøj (DK); Lise Giehm, Frederiksberg (DK)

(73) Assignee: Zealand Pharma A/S, Søborg (DK)

( * ) Notice: Subject to any disclaimer, the term of this patent is extended or adjusted under 35 U.S.C. 154(b) by 560 days.

(21) Appl. No.: 14/417,074

(22) PCT Filed: Jul. 23, 2013

(86) PCT No.: PCT/EP2013/065519
§ 371 (c)(1),
(2) Date: Jan. 23, 2015

(87) PCT Pub. No.: WO2014/016300
PCT Pub. Date: Jan. 30, 2014

(65) Prior Publication Data
US 2015/0210744 A1    Jul. 30, 2015

Related U.S. Application Data

(60) Provisional application No. 61/785,611, filed on Mar. 14, 2013, provisional application No. 61/674,706, filed on Jul. 23, 2012.

(30) Foreign Application Priority Data

Jun. 14, 2013 (DK) .................. PA 2013 00360

(51) Int. Cl.
C07K 14/605 (2006.01)
A61K 38/26 (2006.01)
A61K 38/00 (2006.01)

(52) U.S. Cl.
CPC ............ *C07K 14/605* (2013.01); *A61K 38/26* (2013.01); *A61K 38/00* (2013.01)

(58) Field of Classification Search
CPC ....... C07K 14/605; A61K 38/26; A61K 38/00
See application file for complete search history.

(56) References Cited

U.S. PATENT DOCUMENTS

| | | | |
|---|---|---|---|
| 7,994,122 B2 | 8/2011 | Riber et al. |
| 8,642,540 B2 | 2/2014 | Meier et al. |
| 8,642,541 B2 | 2/2014 | Meier et al. |
| 8,680,049 B2 | 3/2014 | Meier et al. |
| 8,685,919 B2 | 4/2014 | Meier et al. |
| 9,156,901 B2 | 10/2015 | Riber et al. |
| 9,169,310 B2 | 10/2015 | Riber et al. |
| 9,180,169 B2 | 11/2015 | Tolborg et al. |
| 9,403,894 B2 | 8/2016 | Meier et al. |
| 9,896,495 B2 | 2/2018 | Riber et al. |
| 2005/0070469 A1 | 3/2005 | Bloom et al. |
| 2010/0099601 A1 | 4/2010 | Weiss |
| 2010/0190701 A1 | 7/2010 | Day et al. |
| 2010/0240883 A1 | 9/2010 | Wu et al. |
| 2011/0230397 A1 | 9/2011 | Carriero et al. |
| 2011/0286981 A1 | 11/2011 | Meier et al. |
| 2011/0286982 A1 | 11/2011 | Meier et al. |
| 2011/0293586 A1 | 12/2011 | Meier et al. |
| 2011/0293587 A1 | 12/2011 | Meier et al. |
| 2012/0178670 A1 | 7/2012 | Riber et al. |
| 2013/0053304 A1 | 2/2013 | Wang et al. |
| 2013/0157929 A1 | 6/2013 | Riber et al. |
| 2013/0157935 A1 | 6/2013 | Meier et al. |
| 2013/0157953 A1 | 6/2013 | Petersen et al. |
| 2013/0316941 A1 | 11/2013 | Hamprecht et al. |
| 2014/0011733 A1 | 1/2014 | Fosgerau et al. |
| 2014/0080757 A1 | 3/2014 | Tolborg et al. |
| 2014/0127174 A1 | 5/2014 | Meier et al. |
| 2014/0127175 A1 | 5/2014 | Meier et al. |
| 2015/0080295 A1 | 3/2015 | Meier et al. |
| 2015/0111817 A1 | 4/2015 | Riber et al. |
| 2015/0111826 A1 | 4/2015 | Riber et al. |
| 2015/0299281 A1 | 10/2015 | Just et al. |
| 2015/0322130 A1 | 11/2015 | DiMarchi et al. |
| 2015/0376257 A1 | 12/2015 | Riber et al. |
| 2016/0000883 A1 | 1/2016 | Fosgerau et al. |
| 2016/0009777 A1 | 1/2016 | Tolborg et al. |
| 2016/0120951 A1 | 5/2016 | Riber et al. |
| 2016/0304576 A1 | 10/2016 | Meier et al. |
| 2016/0347813 A1 | 12/2016 | Hamprecht et al. |

FOREIGN PATENT DOCUMENTS

| | | |
|---|---|---|
| CN | 101519446 A | 9/2009 |
| DE | 102008003566 A1 | 7/2009 |
| DE | 102008003568 A1 | 7/2009 |
| EP | 0082731 A1 | 6/1983 |
| EP | 2025684 A1 | 2/2009 |
| JP | 2011-524418 A | 9/2011 |

(Continued)

OTHER PUBLICATIONS

Unson et al., Jl. Biol. Chem. 273/17, 10308-10312 (1998) (supplied in Mar. 30, 2017 IDS).*
Hruby et al., Curr. Med. Chem—Imm., Endoc. & Metab. Agents, 199-215 (2001) (supplied in Mar. 30, 2017 IDS).*
Hansson, "Inflammation, atherosclerosis, and coronary artery disease," N Engl J Med. 352(16):1685-95 (2005).
Abbrecht et al., "Erythrocyte life-span in mice acclimatized to different degrees of hypoxia," J Appl Physiol. 32(4):443-445 (1972).
Adelhorst et al., "Structure-activity studies of glucagon-like peptide-1," J Biol Chem 269(9):6275-6278 (1994).
Ali et al., "Cardiomyocyte glucagon receptor signaling modulates outcomes in mice with experimental myocardial infarction," Mol Metab. 4(2):132-143 (2015).
Altschul et al., "Local alignment statistics," Methods Enzymol. 266:460-480 (1996).

(Continued)

*Primary Examiner* — Karlheinz R. Skowronek
*Assistant Examiner* — Joseph Fischer
(74) *Attorney, Agent, or Firm* — Clark & Elbing LLP

(57) ABSTRACT

The present invention relates to glucagon analogs and their medical use, for example in the treatment of hypoglycaemia. In particular, the present invention relates to stable glucagon analogs suitable for use in a liquid formulation.

2 Claims, 1 Drawing Sheet
Specification includes a Sequence Listing.

(56) References Cited

FOREIGN PATENT DOCUMENTS

| | | |
|---|---|---|
| JP | 2012-511900 A | 5/2012 |
| WO | WO-98/08871 A1 | 3/1998 |
| WO | WO-98/11125 A1 | 3/1998 |
| WO | WO-98/11126 A1 | 3/1998 |
| WO | WO-99/25727 A2 | 5/1999 |
| WO | WO-99/46283 A1 | 9/1999 |
| WO | WO-00/34331 A2 | 6/2000 |
| WO | WO-00/55119 A1 | 9/2000 |
| WO | WO-00/55184 A1 | 9/2000 |
| WO | WO-01/04156 A1 | 1/2001 |
| WO | WO-03/022304 A1 | 3/2003 |
| WO | WO-03/053339 A2 | 7/2003 |
| WO | WO-03/053460 A1 | 7/2003 |
| WO | WO-2004/062685 A2 | 7/2004 |
| WO | WO-2004/096854 A2 | 11/2004 |
| WO | WO-2006/051110 A2 | 5/2006 |
| WO | WO-2006/097537 A2 | 9/2006 |
| WO | WO-2006/121860 A2 | 11/2006 |
| WO | WO-2006/134340 A2 | 12/2006 |
| WO | WO-2007/024899 A2 | 3/2007 |
| WO | WO-2007/056362 A2 | 5/2007 |
| WO | WO-2007/081824 A2 | 7/2007 |
| WO | WO-2007/100535 A2 | 9/2007 |
| WO | WO-2008/010101 A2 | 1/2008 |
| WO | WO-2008/071972 A1 | 6/2008 |
| WO | WO-2008/086086 A2 | 7/2008 |
| WO | WO-2008/101017 A2 | 8/2008 |
| WO | WO-2008/152403 A1 | 12/2008 |
| WO | WO-2009/067636 A2 | 5/2009 |
| WO | WO-2009/087081 A2 | 7/2009 |
| WO | WO-2009/087082 A2 | 7/2009 |
| WO | WO-2009/129250 A2 | 10/2009 |
| WO | WO-2009/132129 A2 | 10/2009 |
| WO | WO-2009/152128 A1 | 12/2009 |
| WO | WO-2009/155257 A1 | 12/2009 |
| WO | WO-2009/155258 A2 | 12/2009 |
| WO | WO-2009155257 A1 * | 12/2009 ........... C07K 14/605 |
| WO | WO-2010/002283 A9 | 1/2010 |
| WO | WO-2010/011439 A2 | 1/2010 |
| WO | WO-2010/014946 A2 | 2/2010 |
| WO | WO-2010/016940 A2 | 2/2010 |
| WO | WO-2010/029159 A1 | 3/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | WO-2010070252 A1 * | 6/2010 ........... C07K 14/605 |
| WO | WO-2010/080606 A1 | 7/2010 |
| WO | WO-2010/080609 A1 | 7/2010 |
| WO | WO-2010/148089 A1 | 12/2010 |
| WO | WO-2011/006497 A1 | 1/2011 |
| WO | WO-2011/080103 A1 | 7/2011 |
| WO | WO-2011/088837 A1 | 7/2011 |
| WO | WO-2011/094337 A1 | 8/2011 |
| WO | WO-2011/117416 A1 | 9/2011 |
| WO | WO 2011/117417 * | 9/2011 ........... C07K 14/605 |
| WO | WO-2011/117417 A1 | 9/2011 |
| WO | WO-2011/119657 A1 | 9/2011 |
| WO | WO-2011/160630 A2 | 12/2011 |
| WO | WO-2011/160633 A1 | 12/2011 |
| WO | WO-2012/062803 A1 | 5/2012 |
| WO | WO-2012/062804 A1 | 5/2012 |
| WO | WO-2012/098462 A1 | 7/2012 |
| WO | WO-2012/130866 A1 | 10/2012 |
| WO | WO-2012/140117 A1 | 10/2012 |
| WO | WO-2012/150503 A2 | 11/2012 |
| WO | WO-2012/153196 A2 | 11/2012 |
| WO | WO-2012/167744 A1 | 12/2012 |
| WO | WO-2013/041678 A1 | 3/2013 |
| WO | WO-2013/092703 A2 | 6/2013 |
| WO | WO-2013/164483 A1 | 11/2013 |
| WO | WO-2014/041195 A1 | 3/2014 |
| WO | WO-2015/067715 A2 | 5/2015 |
| WO | WO-2015/124612 A1 | 8/2015 |
| WO | WO-2016/166289 A1 | 10/2016 |

OTHER PUBLICATIONS

Arnold, "Heart failure," <http://www.merckmanuals.com/home/heart_and_blood_vessel_disorders/heart_failure/heart_failure.html?qt=congestive heart failure&alt=sh>, retrieved on Feb. 8, 2015 (12 pages).

Authier et al., "Endosomal proteolysis of glucagon at neutral pH generates the bioactive degradation product miniglucagon-(19-29)," Endocrinology. 144(12):5353-5364 (2003).

Bell, "Heart failure: the frequent, forgotten, and often fatal complication of diabetes," Diabetes Care. 26(8):2433-41 (2003).

Blache et al., "Endopeptidase from rat liver membranes, which generates miniglucagon from glucagon," J Biol Chem. 268(29):21748-21753 (1993).

Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).

Chan et al., "Suppression of weight gain by glucagon in obese Zucker rats," Exp Mol Path. 40(3):320-327 (1984).

Cohen et al., "Oxyntomodulin suppresses appetite and reduces food intake in humans," J Clin Endocrinol Metab. 88(10):4696-4701 (2003).

Communication from the European Patent Office for European Patent Application No. 08875673.9, dated Jul. 4, 2012 (6 pages).

Dakin et al., "Oxyntomodulin inhibits food intake in the rat," Endocrinology. 142(10):4244-4250 (2001).

Dakin et al., "Peripheral oxyntomodulin reduces food intake and body weight gain in rats," Endocrinology. 145(6):2687-2695 (2004).

Day et al., "A new glucagon and GLP-1 co-agonist eliminates obesity in rodents," Nat Chem Biol. 5(10):749-757 (2009).

Delgado et al., "The uses and properties of PEG-linked proteins," Crit Rev Ther Drug Carrier Syst. 9(3,4):249-304 (1992).

Diamant et al., "Diabetic cardiomyopathy in uncomplicated type 2 diabetes is associated with the metabolic syndrome and systemic inflammation," Diabetologia 48(8):1669-70 (2005).

Druce et al., "Investigation of structure-activity relationships of Oxyntomodulin (Oxm) using Oxm analogs," Endocrinology. 150(4):1712-1721 (2009).

Ebert et al., "Gastric inhibitory polypeptide," Clin Gastroenterol. 9(3):679-98 (1980).

England et al., "Glucagon carboxyl-terminal derivatives: Preparation, purification and characterization," Biochemistry. 21(5):940-950 (1982).

European Search Report from European Patent Application No. 07016032.0, dated Jan. 28, 2008 (8 pages).

Finan et al., "Reappraisal of GIP Pharmacology for Metabolic Diseases," Trends Mol Med. 22(5):359-76 (2016).

First Examination Report for New Zealand Patent Application No. 702333, dated Jun. 2, 2016 (4 pages).

Francis et al., "PEGylation of cytokines and other therapeutic proteins and peptides: the importance of biological optimisation of coupling techniques," Int J Hematol. 68(1):1-18 (1998).

Frandsen et al., "Glucagon: structure-function relationships investigated by sequence deletions," Hoppe Seylers Z Physiol Chem. 362(6):665-677 (1981).

Gault et al., "Administration of an acylated GIP-1 and GIP preparation provides added beneficial glucose-lowering and insulinotropic actions over single incretins in mice with Type 2 diabetes and obesity," Clin Sci (Lond). 121(3):107-17 (2011).

Gelfanov et al., Discovery and structural optimization of high affinity co-agonists at the glucagon and GLP-1 receptors. Understanding Biology Using Peptides. Sylvie E. Blondelle, 763-764 (2005).

Goldstein et al., "Effects of chronic heart failure on the capacity of glucagon to enhance contractility and adenyl cyclase activity of human papillary muscles," Circulation. 44(4):638-648 (1971).

(56) References Cited

OTHER PUBLICATIONS

Gombotz et al. "Biodegradable polymers for protein and peptide drug delivery," Bioconjug Chem. 6(4):332-351 (1995).
Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Hjorth et al., "Glucagon and glucagon-like peptide 1: Selective receptor recognition via distinct peptide epitopes," J Biol Chem. 269(48):30121-30124 (1994).
Hostrup et al., Modification of Peptides and Proteins. Delivery Technologies for Biopharmaceuticals: Peptides, Proteins, Nucleic Acids and Vaccines. Jorgensen, Nielsen, 171-91 (2009).
Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
International Preliminary Report on Patentability for PCT/EP2013/069286, completed Jan. 19, 2015 (40 pages).
International Preliminary Report on Patentability for PCT/GB2008/002041, dated Dec. 17, 2009 (7 pages).
International Search Report and Written Opinion for PCT/EP2013/059319, dated Sep. 12, 2013 (12 pages).
International Search Report and Written Opinion for PCT/EP2013/065519, dated Dec. 6, 2013 (11 pages).
International Search Report and Written Opinion for PCT/EP2013/069286, dated Dec. 18, 2013 (16 pages).
International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for International Application No. PCT/DK2010/000099, dated Dec. 2, 2010 (2 pages).
International Search Report for International Application No. PCT/DK2011/000067, dated Dec. 9, 2011 (4 pages).
International Search Report for International Application No. PCT/I132012/000134, dated Jun. 25, 2012 (3 pages).
International Search Report for PCT/DK2011/000072, dated Dec. 6, 2011 (3 pages).
International Search Report for PCT/GB2008/002041, dated Sep. 9, 2008 (3 pages).
International Search Report for PCT/GB2008/004157, dated Jun. 4, 2009 (21 pages).
Irwin et al., "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biol Chem. 386(7):679-87 (2005).
Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).
Jaya et al., "Mechanism of hypocholesterolemic action of glucagon," J Biosci. 12(2):111-4 (1987).
Joshi et al., "The estimation of glutaminyl deamidation and aspartyl cleavage rates in glucagon," Int J Pharm. 273(1-2):213-219 (2004).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Knudsen et al., "Potent derivatives of glucagon-like peptide-1 with pharmacokinetic properties suitable for once daily administration," J Med Chem. 43(9):1664-1669 (2000).
Lefébvre, "The intriguing diversity of the glucagon gene products," Curr Diab Rep. 2(3):201-2 (2002).
Lvoff et al., "Glucagon in heart failure and in cardiogenic shock. Experience in 50 patients," Circulation. 45(3):534-42 (1972).
Madsen et al., "Structure-activity and protraction relationship of long-acting glucagon-like peptide-1 derivatives: importance of fatty acid length, polarity, and bulkiness," J Med Chem. 50(54):6126-6132 (2007).
Malde et al., "Understanding interactions of gastric inhibitory polypeptide (GIP) with its G-protein coupled receptor through NMR and molecular modeling," J Pept Sci. 13(5):287-300 (2007).
Manhart et al., "Structure-function analysis of a series of novel GIP analogues containing different helical length linkers," Biochemistry. 42(10):3081-8 (2003).
Matsumoto et al., "Plasma Incretin Levels and Dipeptidyl Peptidase-4 Activity in Patients with Obstructive Sleep Apnea," Ann Am Thorac Soc. 13(8):1378-87 (2016).
McKee et al., "Receptor binding and adenylate cyclase activities of glucagon analogues modified in the N-terminal region," Biochemistry. 25(7):1650-1656 (1986).
Mehta, "Diabetic cardiomyopathy: insights into pathogenesis, diagnostic challenges, and therapeutic options," Intl J Pharm Sci Res. 3(10):3565-3576 (2012).
NCBI Blast for Accession No. 721913A, retrieved on Dec. 15, 2009 (1 page).
Pan et al., "Design of a long acting peptide functioning as both a glucagon-like peptide-1 receptor agonist and a glucagon receptor antagonist," J Biol Chem. 281(18):12506-12515 (2006).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Parlevliet et al., "Oxyntomodulin ameliorates glucose intolerance in mice fed a high-fat diet," Am J Physiol Endocrinol Metab. 294(1):E142-E147 (2008).
Pocai, "Glucagon signaling in the heart: activation or inhibition?," Mol Metab. 4(2):81-2 (2015).
Pratesi et al., "Poly-L-aspartic acid as a carrier for doxorubicin: a comparative in vivo study of free and polymer-bound drug," Br J Cancer. 52(6):841-848 (1985).
Protest of U.S. Appl. No. 12/664,534 Pursuant 37 CFR 1.291, dated Jan. 13, 2010 (14 pages).
Rose et al., "Insulin proteinase liberates from glucagon a fragment known to have enhanced activity against Ca2+ + Mg2+-dependent ATPase," Biochem J. 256(3):847-51 (1988).
Runge et al., "Differential structural properties of GLP-1 and exendin-4 determine their relative affinity for the GLP-1 receptor N-terminal extracellular domain," Biochemistry. 46(19):5830-40 (2007).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-10312 (1998).
Written Opinion for PCT/DK2011/000072, dated Dec. 6, 2011 (6 pages).
Written Opinion for Singapore Application No. 201209089-0, dated Nov. 8, 2013 (10 pages).
Written Opinion of the International Searching Authority for PCT/GB2008/002041, dated Sep. 9, 2008 (6 pages).

(56) References Cited

OTHER PUBLICATIONS

Zalipsky, "Functionalized poly(ethylene glycol) for preparation of biologically relevant conjugates," Bioconjug Chem. 6(2):150-165 (1995).
Zhu et al.,"The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).
Office Action for Colombian Application No. 16089238, dated Sep. 13, 2017 (18 pages).
Periasamy et al., "Molecular basis of diastolic dysfunction," available in PMC Jul. 6, 2009, published in final edited form as: Heart Fail Clin. 4(1):13-21 (2008) (13 pages).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Unson et al., "Positively charged residues at positions 12, 17, and 18 of glucagon ensure maximum biological potency," J Biol Chem. 273(17):10308-12 (1998).
Chabenne et al., "Optimization of the native glucagon sequence for medicinal purposes," J Diabetes Sci Technol. 4(6):1322-31 (2010).
Bowie et al., "Deciphering the message in protein sequences: tolerance to amino acid substitutions," Science. 247(4948):1306-10 (1990).
Burgess et al., "Possible dissociation of the heparin-binding and mitogenic activities of heparin-binding (acidic fibroblast) growth factor-1 from its receptor-binding activities by site-directed mutagenesis of a single lysine residue," J. Cell Biol. 111, 2129-38, 1990.
Bork, "Powers and pitfalls in sequence analysis: the 70% hurdle," Genome Research 10, 398-400, 2000.
Lazar et al., "Transforming growth factor alpha: mutation of aspartic acid 47 and leucine 48 results in different biological activities," Mol. Cell. Biol. 8, 1247-52, 1988.
U.S. Appl. No. 15/852,458, filed Dec. 22, 2017 (57 pages).
Sturm et al., "Structure-function studies on positions 17, 18, and 21 replacement analogues of glucagon: the importance of charged residues and salt bridges in glucagon biological activity," J Med Chem. 41(15):2693-700 (1998).
Matsuyama, "Glucagon and diabetes," Shijonawate Gakuen Bulletin of Faculty of Rehabilitation. 7:1-12 (2011).
English translation of Notice of Reasons for Rejection from Office Action for Japanese Application No. 2015-523532, dated Apr. 24, 2018 (8 pages).
Kawashima et al., "Case of pancreatic diabetes with improvement in carbohydrate and lipid metabolism brought about by injections of a small quantity of glucagon," The Journal of the Japanese Society of Internal Medicine. 88(2):336-8 (1999).

\* cited by examiner

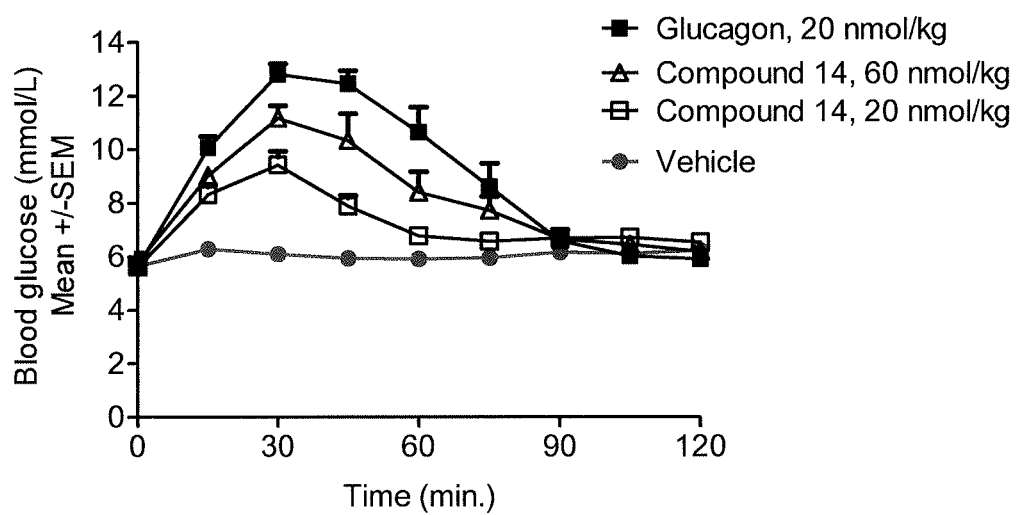

SEQUENCE LISTING

```
<160> NUMBER OF SEQ ID NOS: 44

<210> SEQ ID NO 1
<211> LENGTH: 29
<212> TYPE: PRT
<213> ORGANISM: Homo sapiens

<400> SEQUENCE: 1

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 2
<211> LENGTH: 29
<212> TYPE: PRT
<213> ORGANISM: Artificial sequence
<220> FEATURE:
<223> OTHER INFORMATION: Synthetic compound

<400> SEQUENCE: 2

His Ser Gln Gly Thr Phe Thr Ser Asp Tyr Ser Lys Tyr Leu Asp Ser
1               5                   10                  15

Ala Arg Ala Glu Ser Phe Val Lys Trp Leu Glu Ser Thr
            20                  25

<210> SEQ ID NO 3
<211> LENGTH: 29
<212> TYPE: PRT
<213> ORGANISM: Artificial sequence
<220> FEATURE:
<223> OTHER INFORMATION: Synthetic compound

<400> SEQUENCE: 3

His Ser Gln Gly Thr Phe Thr Ser Asp Tyr Ser Lys Tyr Leu Asp Ser
1               5                   10                  15

Ala Arg Ala Glu Asp Phe Val Lys Trp Leu Glu Glu Thr
            20                  25

<210> SEQ ID NO 4
<211> LENGTH: 29
<212> TYPE: PRT
<213> ORGANISM: Artificial sequence
<220> FEATURE:
<223> OTHER INFORMATION: Synthetic compound
```

<400> SEQUENCE: 4

His Ser Gln Gly Thr Phe Thr Ser Asp Tyr Ser Lys Tyr Leu Asp Lys
1               5                   10                  15

Ala Arg Ala Glu Asp Phe Val Lys Trp Leu Glu Ser Thr
            20                  25

<210> SEQ ID NO 5
<211> LENGTH: 29
<212> TYPE: PRT
<213> ORGANISM: Artificial sequence
<220> FEATURE:
<223> OTHER INFORMATION: Synthetic compound

<400> SEQUENCE: 5

His Ser Gln Gly Thr Phe Thr Ser Asp Tyr Ser Lys Tyr Leu Asp Ser
1               5                   10                  15

Ala Arg Ala Glu Asp Phe Val Ala Trp Leu Glu Ser Thr
            20                  25

<210> SEQ ID NO 6
<211> LENGTH: 29
<212> TYPE: PRT
<213> ORGANISM: Artificial sequence
<220> FEATURE:
<223> OTHER INFORMATION: Synthetic compound

<400> SEQUENCE: 6

His Ser Gln Gly Thr Phe Thr Ser Asp Tyr Ser Lys Tyr Leu Asp Glu
1               5                   10                  15

Ala Arg Ala Lys Asp Phe Val Glu Trp Leu Glu Lys Thr
            20                  25

<210> SEQ ID NO 7
<211> LENGTH: 29
<212> TYPE: PRT
<213> ORGANISM: Artificial sequence
<220> FEATURE:
<223> OTHER INFORMATION: Synthetic compound

<400> SEQUENCE: 7

His Ser Gln Gly Thr Phe Thr Ser Asp Tyr Ser Lys Tyr Leu Asp Ser
1               5                   10                  15

Ala Arg Ala Glu Asp Phe Val Glu Trp Leu Glu Ser Thr
            20                  25

<210> SEQ ID NO 8
<211> LENGTH: 29
<212> TYPE: PRT
<213> ORGANISM: Artificial sequence
<220> FEATURE:
<223> OTHER INFORMATION: Synthetic compound

<400> SEQUENCE: 8

His Ser Gln Gly Thr Phe Thr Ser Asp Tyr Ser Arg Tyr Leu Glu Ser
1               5                   10                  15

Ala Arg Ala Glu Asp Phe Val Lys Trp Leu Glu Ser Thr
            20                  25

<210> SEQ ID NO 9
<211> LENGTH: 29
<212> TYPE: PRT
<213> ORGANISM: Artificial sequence
<220> FEATURE:
<223> OTHER INFORMATION: Synthetic compound

```
<400> SEQUENCE: 9

His Ser Gln Gly Thr Phe Thr Ser Asp Tyr Ser Lys Tyr Leu Glu Ser
1               5                   10                  15

Ala Arg Ala Glu Asp Phe Val Lys Trp Leu Glu Ser Thr
            20                  25

<210> SEQ ID NO 10
<211> LENGTH: 29
<212> TYPE: PRT
<213> ORGANISM: Artificial sequence
<220> FEATURE:
<223> OTHER INFORMATION: Synthetic compound

<400> SEQUENCE: 10

His Ser Gln Gly Thr Phe Thr Ser Asp Tyr Ser Lys Tyr Leu Asp Ser
1               5                   10                  15

Ala Arg Ala Glu Glu Phe Val Lys Trp Leu Glu Ser Thr
            20                  25

<210> SEQ ID NO 11
<211> LENGTH: 29
<212> TYPE: PRT
<213> ORGANISM: Artificial sequence
<220> FEATURE:
<223> OTHER INFORMATION: Synthetic compound

<400> SEQUENCE: 11

His Ser Gln Gly Thr Phe Thr Ser Asp Tyr Ser Lys Tyr Leu Asp Ser
1               5                   10                  15

Ala Arg Ala Glu Asp Phe Val Ser Trp Leu Glu Ser Thr
            20                  25

<210> SEQ ID NO 12
<211> LENGTH: 29
<212> TYPE: PRT
<213> ORGANISM: Artificial sequence
<220> FEATURE:
<223> OTHER INFORMATION: Synthetic compound

<400> SEQUENCE: 12

His Ser Gln Gly Thr Phe Thr Ser Asp Leu Ser Lys Tyr Leu Asp Ser
1               5                   10                  15

Ala Arg Ala Glu Asp Phe Val Lys Trp Leu Glu Ser Thr
            20                  25

<210> SEQ ID NO 13
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 13

His Ser Gln Gly Thr Phe Thr Ser Asp Tyr Ser Lys Tyr Leu Asp Xaa
1               5                   10                  15

Ala Arg Ala Glu Asp Phe Val Lys Trp Leu Glu Ser Thr
            20                  25

<210> SEQ ID NO 14
```

```
<211> LENGTH: 28
<212> TYPE: PRT
<213> ORGANISM: Artificial sequence
<220> FEATURE:
<223> OTHER INFORMATION: Synthetic compound

<400> SEQUENCE: 14

His Ser Gln Gly Thr Phe Thr Ser Asp Tyr Ser Lys Tyr Leu Asp Ser
1               5                   10                  15
Ala Arg Ala Glu Asp Phe Val Lys Trp Leu Glu Ser
            20                  25

<210> SEQ ID NO 15
<211> LENGTH: 29
<212> TYPE: PRT
<213> ORGANISM: Artificial sequence
<220> FEATURE:
<223> OTHER INFORMATION: Synthetic compound

<400> SEQUENCE: 15

His Ser Gln Gly Thr Phe Thr Ser Asp Tyr Ser Lys Tyr Leu Asp Glu
1               5                   10                  15
Ala Arg Ala Glu Asp Phe Val Lys Trp Leu Glu Ser Thr
            20                  25

<210> SEQ ID NO 16
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 16

His Ser Gln Gly Thr Phe Thr Ser Asp Tyr Ser Lys Tyr Leu Asp Xaa
1               5                   10                  15
Ala Arg Ala Glu Ser Phe Val Lys Trp Leu Glu Ser Thr
            20                  25

<210> SEQ ID NO 17
<211> LENGTH: 29
<212> TYPE: PRT
<213> ORGANISM: Artificial sequence
<220> FEATURE:
<223> OTHER INFORMATION: Synthetic compound

<400> SEQUENCE: 17

His Ser Gln Gly Thr Phe Thr Ser Asp Tyr Ser Lys Tyr Leu Glu Ser
1               5                   10                  15
Ala Arg Ala Glu Ser Phe Val Lys Trp Leu Glu Ser Thr
            20                  25

<210> SEQ ID NO 18
<211> LENGTH: 29
<212> TYPE: PRT
<213> ORGANISM: Artificial sequence
<220> FEATURE:
<223> OTHER INFORMATION: Synthetic compound

<400> SEQUENCE: 18

His Ser Gln Gly Thr Phe Thr Ser Asp Tyr Ser Lys Tyr Leu Asp Leu
1               5                   10                  15
```

Ala Arg Ala Glu Asp Phe Val Lys Trp Leu Glu Ser Thr
            20                  25

<210> SEQ ID NO 19
<211> LENGTH: 29
<212> TYPE: PRT
<213> ORGANISM: Artificial sequence
<220> FEATURE:
<223> OTHER INFORMATION: Synthetic compound

<400> SEQUENCE: 19

His Ser Gln Gly Thr Phe Thr Ser Asp Tyr Ser Lys Tyr Leu Asp Lys
1               5                   10                  15

Arg Arg Ala Glu Asp Phe Val Ser Trp Leu Glu Ser Thr
            20                  25

<210> SEQ ID NO 20
<211> LENGTH: 29
<212> TYPE: PRT
<213> ORGANISM: Artificial sequence
<220> FEATURE:
<223> OTHER INFORMATION: Synthetic compound

<400> SEQUENCE: 20

His Ser Gln Gly Thr Phe Thr Ser Asp Tyr Ser Lys Tyr Leu Asp Val
1               5                   10                  15

Ala Arg Ala Glu Ser Phe Val Lys Trp Leu Glu Ser Thr
            20                  25

<210> SEQ ID NO 21
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 21

His Ala Gln Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 22
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 22

His Ser Gln Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 23
<211> LENGTH: 29
<212> TYPE: PRT

<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (4)..(4)
<223> OTHER INFORMATION: Xaa is D-Ala
<220> FEATURE:
<221> NAME/KEY: MISC_FEATURE
<222> LOCATION: (16)..(16)
<223> OTHER INFORMATION: Xaa is Aib

<400> SEQUENCE: 23

His Ser Gln Xaa Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 24
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 24

His Ser Gln Gly Thr Phe Thr Ser Asp Val Ser Lys Tyr Leu Asp Xaa
1               5                   10                  15

Ala Arg Ala Glu Ser Phe Val Lys Trp Leu Glu Ser Thr
            20                  25

<210> SEQ ID NO 25
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: Xaa is 4-N-Acetyl-2,4-diaminobutyric acid
<220> FEATURE:
<221> NAME/KEY: MISC_FEATURE
<222> LOCATION: (16)..(16)
<223> OTHER INFORMATION: Xaa is Aib

<400> SEQUENCE: 25

His Ser Xaa Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 26
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 26

His Ser Gln Gly Thr Phe Thr Ser Asp Tyr Ser Lys Tyr Leu Asp Xaa

```
                1               5                  10                  15
Arg Arg Ala Glu Ser Phe Val Lys Trp Leu Glu Ser Thr
                20                  25
```

<210> SEQ ID NO 27
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: N-delta-methyl-L-glutamine
<220> FEATURE:
<221> NAME/KEY: MISC_FEATURE
<222> LOCATION: (16)..(16)
<223> OTHER INFORMATION: Xaa is Aib

<400> SEQUENCE: 27

```
His Ser Xaa Gly Thr Phe Thr Ser Asp Tyr Ser Lys Tyr Leu Asp Xaa
1               5                  10                  15

Ala Arg Ala Glu Ser Phe Val Lys Trp Leu Glu Ser Thr
                20                  25
```

<210> SEQ ID NO 28
<211> LENGTH: 29
<212> TYPE: PRT
<213> ORGANISM: Artificial sequence
<220> FEATURE:
<223> OTHER INFORMATION: Synthetic compound

<400> SEQUENCE: 28

```
His Ser Gln Gly Thr Phe Thr Ser Asp Tyr Ser Lys Tyr Leu Asp Glu
1               5                  10                  15

Ala Arg Ala Lys Ser Phe Val Glu Trp Leu Glu Lys Thr
                20                  25
```

<210> SEQ ID NO 29
<211> LENGTH: 29
<212> TYPE: PRT
<213> ORGANISM: Artificial sequence
<220> FEATURE:
<223> OTHER INFORMATION: Synthetic compound

<400> SEQUENCE: 29

```
His Ser Gln Gly Thr Phe Thr Ser Asp Tyr Ser Lys Tyr Leu Asp Glu
1               5                  10                  15

Ala Arg Ala Lys Ser Phe Val Glu Trp Leu Glu Ser Thr
                20                  25
```

<210> SEQ ID NO 30
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 30

```
His Ser Gln Gly Thr Phe Thr Ser Asp Tyr Ser Lys Tyr Leu Asp Xaa
1               5                  10                  15

Ala Arg Ala Lys Ser Phe Val Glu Trp Leu Glu Lys Thr
```

-continued

```
<210> SEQ ID NO 31
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 31

His Ser Gln Gly Thr Phe Thr Ser Asp Tyr Ser Lys Tyr Leu Asp Xaa
1               5                   10                  15

Ala Arg Ala Glu Ser Phe Val Lys Trp Leu Glu Ser Ala
            20                  25

<210> SEQ ID NO 32
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 32

His Ser Gln Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 33
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: Xaa is 4-N-Acetyl-2,4-diaminobutyric acid
<220> FEATURE:
<221> NAME/KEY: MISC_FEATURE
<222> LOCATION: (16)..(16)
<223> OTHER INFORMATION: Xaa is Aib

<400> SEQUENCE: 33

His Ser Xaa Gly Thr Phe Thr Ser Asp Tyr Ser Lys Tyr Leu Asp Xaa
1               5                   10                  15

Ala Arg Ala Glu Ser Phe Val Lys Trp Leu Glu Ser Thr
            20                  25

<210> SEQ ID NO 34
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 34
```

His Ser Gln Gly Thr Phe Thr Ser Asp Tyr Ser Lys Tyr Leu Asp Xaa
1               5                   10                  15

Ala Arg Ala Glu Glu Phe Val Ser Trp Leu Glu Lys Thr
            20                  25

<210> SEQ ID NO 35
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 35

His Ser Gln Gly Thr Phe Thr Ser Asp Tyr Ser Lys Tyr Leu Asp Xaa
1               5                   10                  15

Ala Arg Ala Glu Lys Phe Val Glu Trp Leu Glu Ser Thr
            20                  25

<210> SEQ ID NO 36
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 36

His Ser Gln Gly Thr Phe Thr Ser Asp Tyr Ser Lys Tyr Leu Asp Xaa
1               5                   10                  15

Ala Arg Ala Glu Glu Phe Val Ala Trp Leu Glu Ser Thr
            20                  25

<210> SEQ ID NO 37
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 37

His Ser Gln Gly Thr Phe Thr Ser Asp Tyr Ser Lys Tyr Leu Asp Xaa
1               5                   10                  15

Ala Arg Ala Glu Glu Phe Val Lys Trp Leu Glu Glu Thr
            20                  25

<210> SEQ ID NO 38
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 38

His Ser Gln Gly Thr Phe Thr Ser Asp Tyr Ser Lys Tyr Leu Glu Xaa
1               5                   10                  15

Ala Arg Ala Glu Glu Phe Val Lys Trp Leu Glu Ser Thr
            20                  25

<210> SEQ ID NO 39
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (16)..(16)
<223> OTHER INFORMATION: Xaa is Aib

<400> SEQUENCE: 39

His Ser His Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 40
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: Xaa is 4-N-Acetyl-2,4-diaminobutyric acid
<220> FEATURE:
<221> NAME/KEY: MISC_FEATURE
<222> LOCATION: (16)..(16)
<223> OTHER INFORMATION: Xaa is Aib

<400> SEQUENCE: 40

His Ser Xaa Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 41
<211> LENGTH: 29
<212> TYPE: PRT
<213> ORGANISM: Artificial sequence
<220> FEATURE:
<223> OTHER INFORMATION: Synthetic compound
<220> FEATURE:
<221> NAME/KEY: MISC_FEATURE
<222> LOCATION: (3)..(3)
<223> OTHER INFORMATION: Xaa is 3-N-Acetyl-2,3-diaminopropionic acid
<220> FEATURE:
<221> NAME/KEY: MISC_FEATURE
<222> LOCATION: (16)..(16)
<223> OTHER INFORMATION: Xaa is Aib

<400> SEQUENCE: 41

His Ser Xaa Gly Thr Phe Thr Ser Asp Tyr Ser Lys Tyr Leu Asp Xaa
1               5                   10                  15

Ala Arg Ala Glu Glu Phe Val Lys Trp Leu Glu Ser Thr
            20                  25

<210> SEQ ID NO 42
<211> LENGTH: 29

```
<212> TYPE: PRT
<213> ORGANISM: Artificial sequence
<220> FEATURE:
<223> OTHER INFORMATION: Synthetic compound

<400> SEQUENCE: 42

His Ser Gln Gly Thr Phe Thr Ser Asp Tyr Ser Lys Tyr Leu Asp Ser
1               5                   10                  15

Ala Arg Ala Glu Asp Phe Val Lys Trp Leu Glu Ser Thr
            20                  25

<210> SEQ ID NO 43
<211> LENGTH: 29
<212> TYPE: PRT
<213> ORGANISM: Artificial sequence
<220> FEATURE:
<223> OTHER INFORMATION: Synthetic compound

<400> SEQUENCE: 43

His Ser Gln Gly Thr Phe Thr Ser Asp Tyr Ser Lys Tyr Leu Glu Ser
1               5                   10                  15

Arg Arg Ala Lys Glu Phe Val Glu Trp Leu Glu Ser Thr
            20                  25

<210> SEQ ID NO 44
<211> LENGTH: 29
<212> TYPE: PRT
<213> ORGANISM: Artificial Sequence
<220> FEATURE:
<223> OTHER INFORMATION: synthetic construct

<400> SEQUENCE: 44

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Glu Asn Thr
            20                  25
```

GLUCAGON ANALOGUES

FIELD OF THE INVENTION

The present invention relates to glucagon analogues and their medical use, for example in the treatment of hypoglycaemia. In particular, the present invention relates to stable glucagon analogues suitable for use in a liquid formulation.

BACKGROUND OF THE INVENTION

Human preproglucagon is a 158 amino acid precursor polypeptide that is differentially processed in the tissues to form a number of structurally related proglucagon-derived peptides, including glucagon (Glu or GCG), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Native glucagon is a 29-amino acid peptide that corresponds to amino acids 53 to 81 of preproglucagon. Glucagon helps maintain the level of glucose in the blood by binding to glucagon receptors on hepatocytes, causing the liver to release glucose—stored in the form of glycogen—through glycogenolysis. As these stores become depleted, glucagon also stimulates the liver to synthesize additional glucose by gluconeogenesis. This glucose is released into the bloodstream, preventing the development of hypoglycaemia.

Owing to the relatively low physical and chemical stability of native glucagon per se, glucagon products that are currently available commercially, and which are intended primarily for use in "rescue" situations for alleviating acute hypoglycaemia in a diabetic subject who has received an excessively high dose of insulin, are provided in the form of freeze-dried, solid preparations intended for reconstitution in an appropriate liquid medium immediately before use. Hypoglycemic subjects may, inter alia, exhibit dizziness and/or confusion, and in some cases may become unconscious or semi-conscious, rendering them unable to carry out or complete the required initial liquid reconstitution and subsequent injection of the glucagon formulation in question. As a result, this reconstitution and injection may have to be performed by another person who is not experienced in processing the product in the limited time available before excessive glucagon aggregation occurs.

Although stabilized analogues of native glucagon in liquid solution are desirable, no stable liquid formulation of any such glucagon analogue is commercially available.

On that basis, it is clear that there is a strong need for glucagon analogues that, in addition to having satisfactorily high activity at the glucagon receptor, are sufficiently soluble (especially at physiological pH, where native glucagon is not) and stable (both physically and chemically) in aqueous liquid medium. These analogues (i) may advantageously be provided in the form of a ready-to-use liquid pharmaceutical formulation adapted for immediate injection, and (ii) may be able to be stored (including carried by the subject or patient in question under ambient conditions) for a satisfactorily long period of time prior to use.

SUMMARY OF THE INVENTION

In some embodiments, the present invention provides a compound having the formula I:

$$R^1—Z—R^2 \quad (I)$$

or a pharmaceutically acceptable salt or solvate thereof; wherein $R^1$ is hydrogen, $C_{1-4}$ alkyl, acetyl, formyl, benzoyl or trifluoroacetyl;

$R^2$ is OH or $NH_2$; and

Z is an amino acid sequence deriving from the sequence of formula Ia:

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Glu-Asn-Thr (SEQ ID NO: 44) (Ia)

and further comprising at least four amino acid substitutions or deletions that are only at amino acid sequence positions (designated by an X) selected from 2, 3, 4, 9, 10, 15, 16, 17, 20, 21, 24, 28 and 29, as follows:

X2 is selected from Aib and Ala;
X3 is selected from His, Pro, Dab(Ac), Dap(Ac) and Gln(Me);
X4 is DAla;
X9 is Glu;
X10 is selected from Val, Leu, N-Me-Tyr and N-Me-DTyr;
X15 is Glu;
X16 is selected from Aib, Lys, Glu, Leu, Val, DVal, Phe, His, Arg, Pro, DPro, N-Me-Ser and N-Me-DSer;
X17 is selected from Ala and Ser;
X20 is selected from Glu and Lys;
X21 is selected from Glu, Lys and Ser;
X24 is selected from Lys, Ser, Glu and Ala;
X28 is selected from Ser, Glu, and Lys, or is absent;
X29 is selected from Ser and Ala, or is absent;
with the proviso that Z is not selected from:

```
                                         (SEQ ID NO: 42)
HSQGTFTSDYSKYLDSARAEDFVKWLEST;
and
                                         (SEQ ID NO: 43)
HSQGTFTSDYSKYLESRRAKEFVEWLEST.
```

In some embodiments, the present invention provides a compound having the formula I:

$$R^1—Z—R^2 \quad (I)$$

or a pharmaceutically acceptable salt or solvate thereof; wherein $R^1$ is hydrogen, $C_{1-4}$ alkyl, acetyl, formyl, benzoyl or trifluoroacetyl;

$R^2$ is OH or $NH_2$; and

Z is an amino acid sequence deriving from the sequence of formula Ia:

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Glu-Asn-Thr (SEQ ID NO: 44) (Ia)

and further comprising at least four amino acid substitutions or deletions that are only at amino acid sequence positions selected from 2, 3, 9, 10, 15, 16, 17, 20, 21, 24, 28 and 29, as follows:

X2 is selected from Aib and Ala;
X3 is selected from His and Pro;
X9 is Glu;
X10 is selected from N-Me-Tyr and N-Me-DTyr;
X15 is Glu;
X16 is selected from Aib, Lys, Glu, Leu, Val, DVal, Phe, His, Arg, Pro, DPro, N-Me-Ser and N-Me-DSer;
X17 is selected from Ala and Ser;

X20 is selected from Glu and Lys;
X21 is selected from Glu, Lys and Ser;
X24 is selected from Lys, Ser, Glu and Ala;
X28 is selected from Ser and Lys, or is absent;
X29 is selected from Ser and Ala, or is absent;
with the proviso that Z is not selected from:

```
                                          (SEQ ID NO: 42)
HSQGTFTSDYSKYLDSARAEDFVKWLEST;
and (SEQ ID NO: 43)
HSQGTFTSDYSKYLESRRAKEFVEWLEST.
```

In some embodiments, the at least four amino acid substitutions or deletions at amino acid sequence positions (designated by an X) selected from 2, 3, 4, 9, 10, 15, 16, 17, 20, 21, 24, 28 and 29 of the compound of formula I are as follows:
X2 is selected from Aib and Ala;
X3 is selected from His and Pro, Dab(Ac), Dap(Ac) and Gln(Me);
X4 is DAla;
X9 is Glu;
X10 is selected from Val, Leu, N-Me-Tyr and N-Me-DTyr;
X15 is Glu;
X16 is selected from Aib, Lys, Glu, Leu, Val, Phe, His and Arg;
X17 is selected from Ala and Ser;
X20 is selected from Glu and Lys;
X21 is selected from Glu, Lys and Ser;
X24 is selected from Lys, Ser, Glu and Ala;
X28 is selected from Ser, Glu, and Lys, or is absent;
X29 is selected from Ser and Ala, or is absent.

In some embodiments, the at least four amino acid substitutions or deletions are at amino acid sequence positions (designated by an X) selected from 2, 3, 4, 10, 15, 16, 17, 20, 21, 24, 28 and 29 of the compound of formula I, and are as follows:
X2 is Ala;
X3 is Dab(Ac), Dap(Ac) and Gln(Me);
X4 is DAla;
X10 is selected from Leu and Val;
X15 is Glu;
X16 is selected from Aib, Lys, Glu, Leu, and Val;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent.

In some embodiments, the at least four amino acid substitutions or deletions are at amino acid sequence positions (designated by an X) selected from 2, 3, 4, 16, 17, 20, 21, 24, 28 and 29 of the compound of formula I, and are as follows:
X2 is Ala;
X3 is Dab(Ac), Dap(Ac), Gln(Me) or His;
X4 is DAla;
X16 is selected from Aib, Lys, Glu;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent.

It will be understood that any individual molecule comprises at least 4 differences from the sequence of formula Ia, which may be any combination of at least 4 substitutions and deletions permitted within the definitions provided.

The peptide sequence Z may have a maximum of 4 substitutions and deletions (taken in combination), a maximum of 5 substitutions and deletions, a maximum of 6 substitutions and deletions, a maximum of 7 substitutions and deletions, a maximum of 8 substitutions and deletions, a maximum of 9 substitutions and deletions, a maximum of 10 substitutions and deletions, a maximum of 11 substitutions and deletions, a maximum of 12 substitutions and deletions, or a maximum of 13 substitutions and deletions compared to the amino acid sequence of Formula Ia.

For example, the compounds may have between 4 and 11 substitutions and deletions, between 6 and 11 substitutions and deletions, between 4 and 9 substitutions and deletions, or between 6 and 9 substitutions and deletions.

The compounds of the invention have glucagon agonist activity.

The compounds of the invention have improved solubility and/or stability as compared to native human glucagon.

Improved solubility may comprise or constitute improved solubility compared to native glucagon at pH 4 (e.g. in 100 mM acetate buffer at pH 4), pH 5 (e.g. in 100 mM acetate buffer at pH 5), pH 6 (e.g. in 100 mM phosphate buffer at pH 6), pH 7 (e.g. in 100 mM phosphate buffer at pH 7), and/or pH 7.5 (e.g. in 100 mM phosphate buffer at pH 7.5). The determination may be performed under the conditions set out in Example 4. A solubility of ≥1 mg/ml may be desirable.

Improved stability may comprise or constitute improved physical stability and/or improved chemical stability as compared to native human glucagon.

Improved physical stability may comprise or constitute reduced tendency to aggregate, e.g. to form either soluble or insoluble aggregates, e.g. fibrils. Aggregation (e.g. fibril formation) may be determined, for example, at a starting concentration of 1 mg/ml dissolved peptide at pH 7.5 and 40° C. Any appropriate time period may be used, e.g. 24 hours, 48 hours or 96 hours. Aggregation may be determined under the conditions set out in Example 5, with or without agitation.

Improved chemical stability may comprise or constitute a reduced tendency to peptide cleavage or degradation in aqueous buffer, typically in the absence of contaminating protease or peptidase activity. Stability may be determined, for example, at a starting concentration of 1 mg/ml dissolved peptide at pH 4.0 or 7.5 and 40° C. The assessment may comprise determining intact peptide remaining after incubation for a suitable time period. This may involve determining intact peptide purity as defined in Example 6. Incubation may be performed for any suitable time period, e.g. 1 day, 7 days or 14 days. Stability may be determined under the conditions set out in Example 6.

Further embodiments of the present invention include, but are not limited to:
a compound, or a pharmaceutically acceptable salt or solvate thereof, of the invention for use in therapy (e.g. in the treatment of acute or chronic hypoglycaemia);
a pharmaceutical composition comprising a compound, or a pharmaceutically acceptable salt or solvate thereof, of the invention and a pharmaceutically acceptable carrier;
a method of treating a disease or condition in a subject in need thereof, the method comprising administering a therapeutically effective amount of a compound, or a pharmaceutically acceptable salt or solvate thereof, of the invention, or a pharmaceutical composition of the invention to the subject;

use of a compound, or a salt or solvate thereof, of the invention, or a pharmaceutical composition of the invention, in the manufacture of a medicament for use in therapy (e.g. in treatment of acute or chronic hypoglycaemia);

a nucleic acid construct (e.g., a DNA or RNA construct) encoding a compound (peptide) or a peptide Z of the invention;

an expression vector comprising such a nucleic acid construct of the invention; and a host cell comprising such a nucleic acid construct or expression vector of the invention.

In some embodiments, a disease or condition to be treated with a compound or method of the invention is selected from the group consisting of: hypoglycaemia, acute hypoglycaemia, chronic hypoglycaemia, type 2 diabetes, impaired glucose tolerance, type 1 diabetes, obesity, coronary heart disease, atherosclerosis, hypertension, dyslipidemia, hepatic steatosis, β-blocker poisoning, insulinoma, and Von Gierkes disease. In particular embodiments, the disease or condition is hypoglycaemia. In certain embodiments, the hypoglycaemia is selected from the group consisting of: diabetic hypoglycaemia, acute insulin-induced hypoglycaemia, non-diabetic hypoglycaemia, reactive hypoglycaemia, fasting hypoglycaemia, drug-induced hypoglycaemia, alcohol-induced hypoglycaemia, gastric bypass-induced hypoglycaemia, and hypoglycaemia occurring during pregnancy.

In some embodiments, the invention includes a compound or pharmaceutically acceptable salt or solvate thereof for the treatment of hypoglycaemia.

BRIEF DESCRIPTION OF THE DRAWINGS

FIG. 1 is a graph showing the effect of a single subcutaneous administration of vehicle (PBS, pH 7.4), human glucagon (20 nmol/kg body weight) or Compound 14 of the invention (20 and 60 nmol/kg body weight), respectively, on blood glucose levels for 120 minutes in anaesthetized, 5-hour-fasted euglycemic male Sprague-Dawley rats. Data are mean values with SEM (n=6/group).

DETAILED DESCRIPTION OF THE INVENTION

Unless otherwise defined herein, scientific and technical terms used in this application shall have the meanings that are commonly understood by those of ordinary skill in the art. Generally, nomenclature used in connection with, and techniques of, chemistry, molecular biology, cell and cancer biology, immunology, microbiology, pharmacology, and protein and nucleic acid chemistry, described herein, are those well known and commonly used in the art.

All publications, patents and published patent applications referred to in this application are specifically incorporated by reference herein. In case of conflict, the present specification, including its specific definitions, will control.

Each embodiment of the invention described herein may be taken alone or in combination with one or more other embodiments of the invention.

Definitions

Unless specified otherwise, the following definitions are provided for specific terms, which are used herein.

Throughout this specification, the word "comprise" or variations such as "comprises" or "comprising" will be understood to imply the inclusion of a stated integer (or components) or group of integers (or components), but not the exclusion of any other integer (or components) or group of integers (or components).

The singular forms "a," "an," and "the" include the plurals unless the context clearly dictates otherwise.

The term "including" is used to mean "including but not limited to." "Including" and "including but not limited to" are used interchangeably.

The terms "patient," "subject," and "individual" may be used interchangeably and refer to either a human or a non-human animal. These terms include mammals such as humans, primates, livestock animals (e.g., bovines, porcines), companion animals (e.g., canines, felines) and rodents (e.g., mice and rats).

In addition to the explanations of the meanings of certain terms or expressions employed in the present specification that are provided in the above, the following definitions/explanations also apply:

The term "pharmaceutically acceptable carrier" includes any of the standard pharmaceutical carriers or diluents, such as those used in compositions or formulations suitable for oral, pulmonary, rectal, nasal, topical, subcutaneous, intramuscular, intravenous, intraperitoneal, intradermal, transdermal or vaginal administration. Pharmaceutically acceptable carriers for therapeutic use are well known in the pharmaceutical art, and are described, for example, in *Remington's Pharmaceutical Sciences*, Mack Publishing Co. (A. R. Gennaro edit. 1985). Liquid compositions often employ unbuffered or buffered aqueous solutions as carriers. For example, sterile saline or phosphate-buffered saline (PBS) at slightly acidic, slightly alkaline or physiological pH may be used. Relevant pH-buffering agents (some of which have already been mentioned above in connection with pharmaceutical compositions) include phosphates, citrate, acetate, tris(hydroxymethyl)aminomethane (TRIS), N-tris(hydroxymethyl)methyl-3-aminopropane-sulfonic acid (TAPS), ammonium bicarbonate, diethanolamine, histidine (which is often a preferred buffer), arginine and lysine, as well as mixtures thereof. The term further encompasses any agents listed in the US Pharmacopeia for use in animals or humans.

The term "pharmaceutically acceptable salt" in the context of the invention refers to a salt that is not harmful to the patient or subject to be treated therewith. Such salts are in general acid addition salts or basic salts. Acid addition salts include salts of inorganic acids and salts of organic acids. Non-limiting examples of suitable acid addition salts include hydrochloride salts, phosphate salts, formate salts, acetate salts, trifluoroacetate salts and citrate salts. Examples of basic salts include salts where the cation is selected from alkali metal ions, such as sodium and potassium, alkaline earth metal ions, such as calcium, as well as substituted ammonium ions, e.g. of the type $NR(R')_3^+$, where R and R' independently designate optionally substituted $C_{1-6}$alkyl, optionally substituted $C_{1-6}$alkenyl, optionally substituted aryl, or optionally substituted heteroaryl. Other examples of pharmaceutically acceptable salts are described in *Remington's Pharmaceutical Sciences*, 17th edition. Ed. Alfonso R. Gennaro (Ed.), Mack Publishing Company, Easton, Pa., U.S.A., 1985 and more recent editions, and in the *Encyclopaedia of Pharmaceutical Technology*.

The term "solvate" in the context of the present invention refers to a complex of defined stoichiometry formed by a solute (in casu a compound, or a pharmaceutically acceptable salt thereof, of the present invention) and a solvent. Relevant solvents (particularly in the case of pharmaceutically acceptable solvates) include, but are not limited to, water, ethanol and acetic acid. Solvates in which the solvent molecule in question is water are generally referred to as "hydrates".

The terms "therapeutically effective amount" and "therapeutically effective dose" as employed in the context of the present invention (notably in the context of a compound of the invention) refer to an amount or a dose sufficient to cure, alleviate, partially arrest or otherwise promote the cure or healing of a given condition (disorder, disease) or injury and, preferably, complications arising therefrom. An amount or dose effective for a particular purpose will depend on the severity of the condition or injury as well as on the body weight and general state of the subject or patient to be treated. Determination of an amount or dose that is appropriate is within the skills of a trained physician (or veterinarian) of ordinary skill.

The term "treatment" (as well as "treating" and other grammatical variants thereof) as employed in the context of the invention refers to an approach for obtaining beneficial or desired clinical results. For the purposes of the present invention, beneficial or desired clinical results include, but are not limited to, alleviation of symptoms, diminishment of extent of disease, stabilization of (i.e. not worsening of) state of disease, delay or slowing of disease progression, amelioration or palliation of disease state, and remission (whether partial or total), whether detectable or undetectable. "Treatment" may also refer to prolongation of survival compared to expected survival in the absence of treatment. "Treatment" is an intervention performed with the intention of preventing the development of, or altering the pathology of, a disorder. Accordingly, "treatment" refers both to therapeutic treatment and to prophylactic or preventative measures. As used in the context of prophylactic or preventative measures, the compound need not completely prevent the development of the disease or disorder. Those in need of treatment include those already suffering from the disorder, as well as those in which development of the disorder is to be prevented. "Treatment" also means inhibition or reduction of an increase in pathology or symptoms (e.g. weight gain or hypoglycaemia) compared to the absence of treatment, and is not necessarily meant to imply complete cessation of the relevant condition.

The term "agonist" as employed in the context of the invention refers to a substance (ligand) that activates the receptor type in question.

Throughout the present specification, the conventional one-letter and three-letter codes for naturally occurring amino acids are used. Unless otherwise indicated, reference is made to the L-isomeric forms of the amino acids referred to herein.

Dab(Ac): 4-N-Acetyl-2,4-diaminobutyric acid, (2S)-4-(Acetylamino)-2-aminobutanoic acid or 4-(acetylamino)-2-aminobutanoic acid (L-form).

Dap(Ac): 3-N-Acetyl-2,3-diaminopropionic acid or 3-(acetylamino)-2-aminopropanoic acid (L-form)

Gln(Me): N-δ-methyl-L-glutamine

N-Me-Tyr: Tyrosine which is methylated at the α-nitrogen

N-Me-DTyr: D-Tyrosine which is methylated at the α-nitrogen

N-Me-Ser: Serine which is methylated at the α-nitrogen

N-Me-DSer: D-Serine which is methylated at the α-nitrogen

Aib: α-aminoisobutyric acid

The term "native glucagon" refers to native human glucagon having the sequence Hy-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO: 1).

Among sequences disclosed herein are sequences incorporating an "Hy-" moiety at the amino terminus (N-terminus) of the sequence, and either an "—OH" moiety or an "—NH$_2$" moiety at the carboxy terminus (C-terminus) of the sequence. In such cases, and unless otherwise indicated, an "Hy-" moiety at the N-terminus of the sequence in question indicates a hydrogen atom [i.e. $R^1$=hydrogen=Hy- in formulas I and Ia; corresponding to the presence of a free primary or secondary amino group at the N-terminus], while an "—OH" or an "—NH$_2$" moiety at the C-terminus of the sequence indicates a hydroxy group [e.g., $R^2$=OH in formulas I and Ia; corresponding to the presence of a carboxy (COOH) group at the C-terminus] or an amino group [e.g., $R^2$=NH$_2$ in formulas I and Ia; corresponding to the presence of an amido (CONH$_2$) group at the C-terminus], respectively. In each sequence of the invention, a C-terminal "—OH" moiety may be substituted for a C-terminal "—NH$_2$" moiety, and vice-versa.

Some embodiments of the present invention relate to compounds having the formula I:

$$R^1—Z—R^2 \quad (I)$$

or a pharmaceutically acceptable salt or solvate thereof; wherein $R^1$ is hydrogen-, $C_{1-4}$ alkyl, acetyl, formyl, benzoyl or trifluoroacetyl;

$R^2$ is —OH or —NH$_2$; and

Z is an amino acid sequence deriving from the sequence of formula Ia:

His-Ser-Gln-Gly-Thr-Phe-Thr-Ser-Asp-Tyr-Ser-Lys-
Tyr-Leu-Asp-Ser-Arg-Arg-Ala-Gln-Asp-Phe-
Val-Gln-Trp-Leu-Glu-Asn-Thr (SEQ ID NO:
44)  (Ia)

and further comprising at least four amino acid substitutions or deletions that are only at sequence positions (designated by an X) selected from 2, 3, 4, 9, 10, 15, 16, 17, 20, 21, 24, 28 and 29, as follows:

X2 is selected from Aib and Ala;

X3 is selected from His, Pro, Dab(Ac), Dap(Ac) and Gln(Me);

X4 is DAla;

X9 is Glu;

X10 is selected from Val, Leu N-Me-Tyr and N-Me-DTyr;

X15 is Glu;

X16 is selected from Aib, Lys, Glu, Leu, Val, DVal, Phe, His, Arg, Pro, DPro, N-Me-Ser and N-Me-DSer;

X17 is selected from Ala and Ser;

X20 is selected from Glu and Lys;

X21 is selected from Glu, Lys and Ser;

X24 is selected from Lys, Ser, Glu and Ala;

X25 is selected from Arg, Lys, His, Ile, Leu, Ala, Met, Cys, Asn, Val, Ser, Glu, Asp, Gln, Thr and (p)Tyr;

X28 is selected from Ser, Lys, and Glu, or is absent;

X29 is selected from Ser and Ala, or is absent; with the proviso that Z is not selected from:

(SEQ ID NO: 42)
HSQGTFTSDYSKYLDSARAEDFVKWLEST;
and (SEQ ID NO: 43)
HSQGTFTSDYSKYLESRRAKEFVEWLEST.

Some embodiments of the present invention relate to compounds having the formula I:

$$R^1\text{—}Z\text{—}R^2 \quad \text{(I)}$$

or a pharmaceutically acceptable salt or solvate thereof; wherein $R^1$ is hydrogen-, $C_{1-4}$ alkyl, acetyl, formyl, benzoyl or trifluoroacetyl;

$R^2$ is —OH or —NH$_2$; and

Z is an amino acid sequence deriving from the sequence of formula Ia:

His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Glu-Asn-Thr (SEQ ID NO: 44) (Ia)

and further comprising at least four amino acid substitutions or deletions that are only at sequence positions (designated by an X) selected from 2, 3, 9, 10, 15, 16, 17, 20, 21, 24, 28 and 29, as follows:
X2 is selected from Aib and Ala;
X3 is selected from His and Pro;
X9 is Glu;
X10 is selected from N-Me-Tyr and N-Me-DTyr;
X15 is Glu;
X16 is selected from Aib, Lys, Glu, Leu, Val, DVal, Phe, His, Arg, Pro, DPro, N-Me-Ser and N-Me-DSer;
X17 is selected from Ala and Ser;
X20 is selected from Glu and Lys;
X21 is selected from Glu, Lys and Ser;
X24 is selected from Lys, Ser, Glu and Ala;
X25 is selected from Arg, Lys, His, Ile, Leu, Ala, Met, Cys, Asn, Val, Ser, Glu, Asp, Gln, Thr and (p)Tyr;
X28 is selected from Ser and Lys, or is absent;
X29 is selected from Ser and Ala, or is absent;
with the proviso that Z is not selected from:

HSQGTFTSDYSKYLDSARAEDFVKWLEST; (SEQ ID NO: 42)
and

HSQGTFTSDYSKYLESRRAKEFVEWLEST. (SEQ ID NO: 43)

In some embodiments, the at least four amino acid substitutions or deletions at amino acid sequence positions (designated by an X) selected from 2, 3, 4, 9, 10, 15, 16, 17, 20, 21, 24, 28 and 29 of the compound of formula I are as follows:
X2 is selected from Aib and Ala;
X3 is selected from His and Pro, Dab(Ac), Dap(Ac) and Gln(Me);
X4 is DAla;
X9 is Glu;
X10 is selected from Val, Leu, N-Me-Tyr and N-Me-DTyr;
X15 is Glu;
X16 is selected from Aib, Lys, Glu, Leu, Val, Phe, His and Arg;
X17 is selected from Ala and Ser;
X20 is selected from Glu and Lys;
X21 is selected from Glu, Lys and Ser;
X24 is selected from Lys, Ser, Glu and Ala;
X28 is selected from Ser, Glu and Lys, or is absent;
X29 is selected from Ser and Ala, or is absent.
In some embodiments, the at least four amino acid substitutions or deletions are at amino acid sequence positions (designated by an X) selected from 2, 3, 4, 10, 15, 16, 17, 20, 21, 24, 28 and 29 of the compound of formula I, and are as follows:
X2 is Ala;
X3 is Dab(Ac) and Gln(Me);
X4 is DAla;
X10 is selected from Leu and Val;
X15 is Glu;
X16 is selected from Aib, Lys, Glu, Leu, and Val;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent. In some embodiments, X3 is selected from Dab(Ac) and Gln(Me).

In some embodiments, the at least four amino acid substitutions or deletions are at amino acid sequence positions (designated by an X) selected from 2, 3, 4, 16, 17, 20, 21, 24, 28 and 29 of the compound of formula I, and are as follows:
X2 is Ala;
X3 is Dab(Ac), Dap(Ac), Gln(Me) or His;
X4 is DAla;
X16 is selected from Aib, Lys, Glu;
X17 is Ala;
X20 is selected from Glu and Lys;
X21 is selected from Glu and Ser;
X24 is selected from Lys, Ser and Glu;
X28 is selected from Ser, Glu and Lys;
X29 is Ala, or is absent.
In some embodiments, X17 is Ala.
In some embodiments, X25 is selected from Arg, His or Lys. In some embodiments, the compounds of the invention may comprise substitutions in position 25, such as those referred to in WO2011/117417, which is incorporated herein by reference. However, such substitutions at position 25 are not necessary in the present invention to obtain enhanced physical stability of the glucagon analogues.
In some embodiments, X27 is selected from Ser, Lys, Glu, and Asp. In some embodiments, X27 is selected from: Glu and Asp. In some embodiments, X27 is Glu.
In some embodiments, X28 and/or X29 may be amino acid residues other than those disclosed above. In some embodiments, the substitution may be a hydrophilic substitution (e.g., Arg, Lys, Asn, His, Gln, Asp, Ser, or Glu). In some embodiments, X28 and/or X29 may be selected from: Glu, Asp, Lys, Arg, Ser, Leu, Ala and Gly. In some embodiments, X28 is Glu or Asp. In some embodiments, X29 is Glu or Asp. In some embodiments, X28 is Glu and X29 is Glu.
In some embodiments, X17 is Ala and X27 is Glu. In some embodiments, X20 is Glu and X27 is Glu. In some embodiments, X17 is Ala, X20 is Glu, and X27 is Glu. In some embodiments, X16 is Aib and X27 is Glu. In some embodiments, X16 is Aib, X21 is Ser, and X27 is Glu. In some embodiments, X16 is Aib, X21 is Ser, X27 is Glu, and X28 is Ser.

In addition to the possibility of substitution of the amino acid residue at position 3 (X3) in formula Ia with an amino acid residue selected from His, Pro, Dab(Ac) and Gln(Me), position 3 may also be substituted with an analogue of glutamine, which will typically be an unnatural amino acid (i.e. one not naturally occurring in mammalian proteins) such as Dap(Ac) [i.e. X3=Dap(Ac)]. Nonetheless, in all of the definitions provided herein, the invention further encompasses compounds defined by the same generic formulae but in which Dap(Ac) is not permitted at X3.

In some embodiments of compounds of the invention, Z is selected from the group consisting of:

HSQGTFTSDYSKYLDSARAESFVKWLEST (SEQ ID NO: 2)

HSQGTFTSDYSKYLDSARAEDFVKWLEET (SEQ ID NO: 3)

HSQGTFTSDYSKYLDKARAEDFVKWLEST (SEQ ID NO: 4)

HSQGTFTSDYSKYLDSARAEDFVAWLEST (SEQ ID NO: 5)

HSQGTFTSDYSKYLDEARAKDFVEWLEKT (SEQ ID NO: 6)

HSQGTFTSDYSKYLDSARAEDFVEWLEST (SEQ ID NO: 7)

HSQGTFTSDYSRYLESARAEDFVKWLEST (SEQ ID NO: 8)

HSQGTFTSDYSKYLESARAEDFVKWLEST (SEQ ID NO: 9)

HSQGTFTSDYSKYLDSARAEEFVKWLEST (SEQ ID NO: 10)

HSQGTFTSDYSKYLDSARAEDFVSWLEST (SEQ ID NO: 11)

HSQGTFTSDLSKYLDSARAEDFVKWLEST (SEQ ID NO: 12)

HSQGTFTSDYSKYLD-Aib-ARAEDFVKWLEST (SEQ ID NO: 13)

HSQGTFTSDYSKYLDSARAEDFVKWLES (SEQ ID NO: 14)

HSQGTFTSDYSKYLDEARAEDFVKWLEST (SEQ ID NO: 15)

HSQGTFTSDYSKYLD-Aib-ARAESFVKWLEST (SEQ ID NO: 16)

HSQGTFTSDYSKYLESARAESFVKWLEST (SEQ ID NO: 17)

HSQGTFTSDYSKYLDLARAEDFVKWLEST (SEQ ID NO: 18)

HSQGTFTSDYSKYLDKRRAEDFVSWLEST (SEQ ID NO: 19)

HSQGTFTSDYSKYLDVARAESFVKWLEST (SEQ ID NO: 20)

HAQGTFTSDYSKYLD-Aib-ARAESFVKWLEST (SEQ ID NO: 21)

HSQGTFTSDYSKYLD-Aib-ARAEEFVKWLEST (SEQ ID NO: 22)

HSQ-DAla-TFTSDYSKYLD-Aib-ARAESFVKWLEST (SEQ ID NO: 23)

HSQGTFTSDVSKYLD-Aib-ARAESFVKWLEST (SEQ ID NO: 24)

HS-[Dab(Ac)]-GTFTSDYSKYLD-Aib-ARAESFVKWLEST (SEQ ID NO: 25)

HSQGTFTSDYSKYLD-Aib-RRAESFVKWLEST (SEQ ID NO: 26)

HS-[Gln(Me)]-GTFTSDYSKYLD-Aib-ARAESFVKWLEST (SEQ ID NO: 27)

HSQGTFTSDYSKYLDEARAKSFVEWLEKT (SEQ ID NO: 28)

HSQGTFTSDYSKYLDEARAKSFVEWLEST (SEQ ID NO: 29)

HSQGTFTSDYSKYLD-Aib-ARAKSFVEWLEKT (SEQ ID NO: 30)

HSQGTFTSDYSKYLD-Aib-ARAESFVKWLESA (SEQ ID NO: 31)

HSQGTFTSDYSKYLD-Aib-ARAESFVKWLEST (SEQ ID NO: 32)

HS-[Dab(Ac)]-GTFTSDYSKYLD-Aib-ARAESFVKWLEST (SEQ ID NO: 33)

HSQGTFTSDYSKYLD-Aib-ARAEEFVSWLEKT (SEQ ID NO: 34)

HSQGTFTSDYSKYLD-Aib-ARAEKFVEWLEST (SEQ ID NO: 35)

HSQGTFTSDYSKYLD-Aib-ARAEEFVAWLEST (SEQ ID NO: 36)

HSQGTFTSDYSKYLD-Aib-ARAEEFVKWLEET (SEQ ID NO: 37)

HSQGTFTSDYSKYLE-Aib-ARAEEFVKWLEST (SEQ ID NO: 38)

HSHGTFTSDYSKYLD-Aib-ARAEEFVKWLEST (SEQ ID NO: 39)

HS-[Dab(Ac)]-GTFTSDYSKYLD-Aib-ARAEEFVKWLEST (SEQ ID NO: 40)

and

HS-[Dap(Ac)]-GTFTSDYSKYLD-Aib-ARAEEFVKWLEST. (SEQ ID NO: 41)

Specific compounds of the invention include:
Hy-HSQGTFTSDYSKYLDSARAESFVKWLEST-OH (SEQ ID NO: 2) Compound 1;
Hy-HSQGTFTSDYSKYLDSARAEDFVKWLEET-OH (SEQ ID NO: 3) Compound 2;
Hy-HSQGTFTSDYSKYLDKARAEDFVKWLEST-OH (SEQ ID NO: 4) Compound 3;
Hy-HSQGTFTSDYSKYLDSARAEDFVAWLEST-OH (SEQ ID NO: 5) Compound 4;
Hy-HSQGTFTSDYSKYLDEARAKDFVEWLEKT-OH (SEQ ID NO: 6) Compound 5;
Hy-HSQGTFTSDYSKYLDSARAEDFVEWLEST-OH (SEQ ID NO: 7) Compound 6;
Hy-HSQGTFTSDYSRYLESARAEDFVKWLEST-OH (SEQ ID NO: 8) Compound 7;
Hy-HSQGTFTSDYSKYLESARAEDFVKWLEST-OH (SEQ ID NO: 9) Compound 8;
Hy-HSQGTFTSDYSKYLDSARAEEFVKWLEST-OH (SEQ ID NO: 10) Compound 9;
Hy-HSQGTFTSDYSKYLDSARAEDFVSWLEST-OH (SEQ ID NO: 11) Compound 10;
Hy-HSQGTFTSDLSKYLDSARAEDFVKWLEST-OH (SEQ ID NO: 12) Compound 11;
Hy-HSQGTFTSDYSKYLD-Aib-ARAEDFVKWLEST-OH (SEQ ID NO: 13) Compound 12;
Hy-HSQGTFTSDYSKYLDSARAEDFVKWLES-OH (SEQ ID NO: 14) Compound 13;
Hy-HSQGTFTSDYSKYLDEARAEDFVKWLEST-OH (SEQ ID NO: 15) Compound 14;
Hy-HSQGTFTSDYSKYLD-Aib-ARAESFVKWLEST-OH (SEQ ID NO: 16) Compound 15;

Hy-HSQGTFTSDYSKYLESARAESFVKWLEST-OH (SEQ ID NO: 17) Compound 16;
Hy-HSQGTFTSDYSKYLDLARAEDFVKWLEST-OH (SEQ ID NO: 18) Compound 17;
Hy-HSQGTFTSDYSKYLDKRRAEDFVSWLEST-OH (SEQ ID NO: 19) Compound 18;
Hy-HSQGTFTSDYSKYLDVARAESFVKWLEST-OH (SEQ ID NO: 20) Compound 19;
Hy-HAQGTFTSDYSKYLD-Aib-ARAESFVKWLEST-OH (SEQ ID NO: 21) Compound 20;
Hy-HSQGTFTSDYSKYLD-Aib-ARAEEFVKWLEST-OH (SEQ ID NO: 22) Compound 21;
Hy-HSQ-DAla-TFTSDYSKYLD-Aib-ARAESFVKWLEST-OH (SEQ ID NO: 23) Compound 22;
Hy-HSQGTFTSDVSKYLD-Aib-ARAESFVKWLEST-OH (SEQ ID NO: 24) Compound 23;
Hy-HS-[Dab(Ac)]-GTFTSDYSKYLD-Aib-ARAESFVKWLEST-NH$_2$ (SEQ ID NO: 25) Compound 24;
Hy-HSQGTFTSDYSKYLD-Aib-RRAESFVKWLEST-OH (SEQ ID NO: 26) Compound 25;
Hy-HS-[Gln(Me)]-GTFTSDYSKYLD-Aib-ARAESFVKWLEST-OH (SEQ ID NO: 27) Compound 26;
Hy-HSQGTFTSDYSKYLDEARAKSFVEWLEKT-OH (SEQ ID NO: 28) Compound 27;
Hy-HSQGTFTSDYSKYLDEARAKSFVEWLEST-OH (SEQ ID NO: 29) Compound 28;
Hy-HSQGTFTSDYSKYLD-Aib-ARAKSFVEWLEKT-OH (SEQ ID NO: 30) Compound 29;
Hy-HSQGTFTSDYSKYLD-Aib-ARAESFVKWLESA-OH (SEQ ID NO: 31) Compound 30;
Hy-HSQGTFTSDYSKYLD-Aib-ARAESFVKWLEST-NH$_2$ (SEQ ID NO: 32) Compound 31;
Hy-HS-[Dab(Ac)]-GTFTSDYSKYLD-Aib-ARAESFVKWLEST-OH (SEQ ID NO: 33) Compound 32;
Hy-HSQGTFTSDYSKYLD-Aib-ARAEEFVSWLEKT-OH (SEQ ID NO: 34) Compound 33;
Hy-HSQGTFTSDYSKYLD-Aib-ARAEKFVEWLEST-OH (SEQ ID NO: 35) Compound 34;
Hy-HSQGTFTSDYSKYLD-Aib-ARAEEFVAWLEST-OH (SEQ ID NO: 36) Compound 35;
Hy-HSQGTFTSDYSKYLD-Aib-ARAEEFVKWLEET-OH (SEQ ID NO: 37) Compound 36;
Hy-HSQGTFTSDYSKYLE-Aib-ARAEEFVKWLEST-OH (SEQ ID NO: 38) Compound 37;
Hy-HSHGTFTSDYSKYLD-Aib-ARAEEFVKWLEST-NH$_2$ (SEQ ID NO: 39) Compound 38;
Hy-HS-[Dab(Ac)]-GTFTSDYSKYLD-Aib-ARAEEFVKWLEST-OH (SEQ ID NO: 40) Compound 39;
Hy-HS-[Dab(Ac)]-GTFTSDYSKYLD-Aib-ARAEEFVKWLEST-NH$_2$ (SEQ ID NO: 40) Compound 40;
Hy-HS-[Dap(Ac)]-GTFTSDYSKYLD-Aib-ARAEEFVKWLEST-NH$_2$ (SEQ ID NO: 41) Compound 41;
and pharmaceutically acceptable salts and solvates thereof.

Each of the latter specific compounds (peptides), and pharmaceutically acceptable salts and solvates thereof, of the invention further constitutes an individual embodiment of the invention. Thus, in one embodiment the compound of the invention is
Hy-HSQGTFTSDYSKYLDSARAESFVKWLEST-OH (SEQ ID NO: 2)
or a pharmaceutically acceptable salt or solvate thereof.
In another embodiment the compound of the invention is
Hy-HSQGTFTSDYSKYLDSARAEDFVKWLEET-OH (SEQ ID NO: 3)
or a pharmaceutically acceptable salt or solvate thereof.
In another embodiment the compound of the invention is
Hy-HSQGTFTSDYSKYLDKARAEDFVKWLEST-OH (SEQ ID NO: 4)
or a pharmaceutically acceptable salt or solvate thereof.
In another embodiment the compound of the invention is
Hy-HSQGTFTSDYSKYLDSARAEDFVAWLEST-OH (SEQ ID NO: 5)
or a pharmaceutically acceptable salt or solvate thereof.
In another embodiment the compound of the invention is
Hy-HSQGTFTSDYSKYLDEARAKDFVEWLEKT-OH (SEQ ID NO: 6)
or a pharmaceutically acceptable salt or solvate thereof.
In another embodiment the compound of the invention is
Hy-HSQGTFTSDYSKYLDSARAEDFVEWLEST-OH (SEQ ID NO: 7)
or a pharmaceutically acceptable salt or solvate thereof.
In another embodiment the compound of the invention is
Hy-HSQGTFTSDYSRYLESARAEDFVKWLEST-OH (SEQ ID NO: 8)
or a pharmaceutically acceptable salt or solvate thereof.
In another embodiment the compound of the invention is
Hy-HSQGTFTSDYSKYLESARAEDFVKWLEST-OH (SEQ ID NO: 9)
or a pharmaceutically acceptable salt or solvate thereof.
In another embodiment the compound of the invention is
Hy-HSQGTFTSDYSKYLDSARAEEFVKWLEST-OH (SEQ ID NO: 10)
or a pharmaceutically acceptable salt or solvate thereof.
In another embodiment the compound of the invention is
Hy-HSQGTFTSDYSKYLDSARAEDFVSWLEST-OH (SEQ ID NO: 11)
or a pharmaceutically acceptable salt or solvate thereof.
In another embodiment the compound of the invention is
Hy-HSQGTFTSDLSKYLDSARAEDFVKWLEST-OH (SEQ ID NO: 12)
or a pharmaceutically acceptable salt or solvate thereof.
In another embodiment the compound of the invention is
Hy-HSQGTFTSDYSKYLD-Aib-ARAEDFVKWLEST-OH (SEQ ID NO: 13)
or a pharmaceutically acceptable salt or solvate thereof.
In another embodiment the compound of the invention is
Hy-HSQGTFTSDYSKYLDSARAEDFVKWLES-OH (SEQ ID NO: 14)
or a pharmaceutically acceptable salt or solvate thereof.
In another embodiment the compound of the invention is
Hy-HSQGTFTSDYSKYLDEARAEDFVKWLEST-OH (SEQ ID NO: 15)
or a pharmaceutically acceptable salt or solvate thereof.
In another embodiment the compound of the invention is
Hy-HSQGTFTSDYSKYLD-Aib-ARAESFVKWLEST-OH (SEQ ID NO: 16)
or a pharmaceutically acceptable salt or solvate thereof.
In another embodiment the compound of the invention is
Hy-HSQGTFTSDYSKYLESARAESFVKWLEST-OH (SEQ ID NO: 17)
or a pharmaceutically acceptable salt or solvate thereof.
In another embodiment the compound of the invention is
Hy-HSQGTFTSDYSKYLDLARAEDFVKWLEST-OH (SEQ ID NO: 18)
or a pharmaceutically acceptable salt or solvate thereof.
In another embodiment the compound of the invention is
Hy-HSQGTFTSDYSKYLDKRRAEDFVSWLEST-OH (SEQ ID NO: 19)
or a pharmaceutically acceptable salt or solvate thereof.
In another embodiment the compound of the invention is
Hy-HSQGTFTSDYSKYLDVARAESFVKWLEST-OH (SEQ ID NO: 20)
or a pharmaceutically acceptable salt or solvate thereof.

In another embodiment the compound of the invention is Hy-HAQGTFTSDYSKYLD-Aib-ARAESFVKWLEST-OH (SEQ ID NO: 21)
or a pharmaceutically acceptable salt or solvate thereof.

In another embodiment the compound of the invention is Hy-HSQGTFTSDYSKYLD-Aib-ARAEEFVKWLEST-OH (SEQ ID NO: 22)
or a pharmaceutically acceptable salt or solvate thereof.

In another embodiment the compound of the invention is Hy-HSQ-DAla-TFTSDYSKYLD-Aib-ARAESFVK-WLEST-OH (SEQ ID NO: 23)
or a pharmaceutically acceptable salt or solvate thereof.

In another embodiment the compound of the invention is Hy-HSQGTFTSDVSKYLD-Aib-ARAESFVKWLEST-OH (SEQ ID NO: 24)
or a pharmaceutically acceptable salt or solvate thereof.

In another embodiment the compound of the invention is Hy-HS-[Dab(Ac)]-GTFTSDYSKYLD-Aib-ARAESFVK-WLEST-NH$_2$ (SEQ ID NO: 25)
or a pharmaceutically acceptable salt or solvate thereof.

In another embodiment the compound of the invention is Hy-HSQGTFTSDYSKYLD-Aib-RRAESFVKWLEST-OH (SEQ ID NO: 26)
or a pharmaceutically acceptable salt or solvate thereof.

In another embodiment the compound of the invention is Hy-HS-[Gln(Me)]-GTFTSDYSKYLD-Aib-ARAESFVK-WLEST-OH (SEQ ID NO: 27)
or a pharmaceutically acceptable salt or solvate thereof.

In another embodiment the compound of the invention is Hy-HSQGTFTSDYSKYLDEARAKSFVEWLEKT-OH (SEQ ID NO: 28)
or a pharmaceutically acceptable salt or solvate thereof.

In another embodiment the compound of the invention is Hy-HSQGTFTSDYSKYLDEARAKSFVEWLEST-OH (SEQ ID NO: 29)
or a pharmaceutically acceptable salt or solvate thereof.

In another embodiment the compound of the invention is Hy-HSQGTFTSDYSKYLD-Aib-ARAKSFVEWLEKT-OH (SEQ ID NO: 30)
or a pharmaceutically acceptable salt or solvate thereof.

In another embodiment the compound of the invention is Hy-HSQGTFTSDYSKYLD-Aib-ARAESFVKWLESA-OH (SEQ ID NO: 31)
or a pharmaceutically acceptable salt or solvate thereof.

In another embodiment the compound of the invention is Hy-HSQGTFTSDYSKYLD-Aib-ARAESFVKWLEST-NH$_2$ (SEQ ID NO: 32)
or a pharmaceutically acceptable salt or solvate thereof.

In another embodiment the compound of the invention is Hy-HS-[Dab(Ac)]-GTFTSDYSKYLD-Aib-ARAESFVK-WLEST-OH (SEQ ID NO: 33)
or a pharmaceutically acceptable salt or solvate thereof.

In another embodiment the compound of the invention is Hy-HSQGTFTSDYSKYLD-Aib-ARAEEFVSWLEKT-OH (SEQ ID NO: 34)
or a pharmaceutically acceptable salt or solvate thereof.

In another embodiment the compound of the invention is Hy-HSQGTFTSDYSKYLD-Aib-ARAEKFVEWLEST-OH (SEQ ID NO: 35)
or a pharmaceutically acceptable salt or solvate thereof.

In another embodiment the compound of the invention is Hy-HSQGTFTSDYSKYLD-Aib-ARAEEFVAWLEST-OH (SEQ ID NO: 36)
or a pharmaceutically acceptable salt or solvate thereof.

In another embodiment the compound of the invention is Hy-HSQGTFTSDYSKYLD-Aib-ARAEEFVKWLEET-OH (SEQ ID NO: 37)
or a pharmaceutically acceptable salt or solvate thereof.

In another embodiment the compound of the invention is Hy-HSQGTFTSDYSKYLE-Aib-ARAEEFVKWLEST-OH (SEQ ID NO: 38)
or a pharmaceutically acceptable salt or solvate thereof.

In yet another embodiment the compound of the invention is
Hy-HSHGTFTSDYSKYLD-Aib-ARAEEFVKWLEST-NH$_2$ (SEQ ID NO: 39)
or a pharmaceutically acceptable salt or solvate thereof.

In another embodiment the compound of the invention is Hy-HS-[Dab(Ac)]-GTFTSDYSKYLD-Aib-ARAEEFVK-WLEST-OH (SEQ ID NO: 40)
or a pharmaceutically acceptable salt or solvate thereof.

In another embodiment the compound of the invention is Hy-HS-[Dab(Ac)]-GTFTSDYSKYLD-Aib-ARAEEFVK-WLEST-NH$_2$ (SEQ ID NO: 40)
or a pharmaceutically acceptable salt or solvate thereof.

In another embodiment the compound of the invention is Hy-HS-[Dap(Ac)]-GTFTSDYSKYLD-Aib-ARAEEFVK-WLEST-NH$_2$ (SEQ ID NO: 41)
or a pharmaceutically acceptable salt or solvate thereof.

Compounds of the invention may have one or more intramolecular bridges within the peptide sequence. Each such bridge is formed between the side-chains of two amino acid residues in the sequence which are typically separated by three other amino acid residues (i.e. between a side-chain of amino acid A and a side-chain of amino acid A+4).

For example, such a bridge may be formed between the side-chains of amino acid residue pairs 12 and 16, 16 and 20, 20 and 24, or 24 and 28. The two side-chains in question may be linked to one another through ionic interactions, or via covalent bonds. Thus, such pairs of amino acid residues may for example contain oppositely charged side-chains capable of forming a salt bridge or resulting in an ionic interaction. In such cases, one of the amino acid residues in question may, for example, be Glu or Asp, while the other may, for example, be Lys or Arg. Pairing of Lys and Glu or Lys and Asp may also lead to formation of a lactam ring.

Pharmaceutical Compositions

In some embodiments, the present invention relates to pharmaceutical compositions comprising a compound (or a pharmaceutically acceptable salt or solvate thereof) of the invention and a pharmaceutically acceptable carrier. Such pharmaceutical compositions may be prepared by conventional techniques, e.g. as described in Remington: *The Science and Practice of Pharmacy*, 19$^{th}$ edition, 1995.

Certain embodiments of liquid pharmaceutical compositions of the invention may comprise a compound of the invention present in a concentration from about 0.01 mg/ml to about 25 mg/ml, such as from about 1 mg/ml to about 10 mg/ml, e.g. from about 1 mg/ml to about 5 mg/ml. In some embodiments, the composition has a pH from 2.0 to 10.0. A pharmaceutical composition of the invention may further comprise a buffer system, preservative(s), isotonicity agent(s), chelating stabilizer(s) and/or surfactant(s). Particularly useful embodiments of liquid pharmaceutical compositions of the invention are aqueous compositions, i.e. compositions comprising water. Such compositions may be in the form of an aqueous solution or an aqueous suspension. Preferred embodiments of aqueous pharmaceutical compositions of the invention are aqueous solutions. In the context of the invention the term "aqueous composition" will normally refer to a composition comprising at least 50% by weight (50% w/w) of water. Likewise, the term "aqueous solution" will normally refer to a solution comprising at least 50% w/w of water, and the term "aqueous suspension" to a suspension comprising at least 50% w/w of water.

In some embodiments, a pharmaceutical composition of the invention comprises an aqueous solution of a compound (or a pharmaceutically acceptable salt or solvate thereof) of the invention present at a concentration of from 0.1 mg/ml or above, together with a buffer, the composition having a pH from about 2.0 to about 10.0, such as a pH from about 6.0 to about 8.5, e.g. from about 6.5 to about 8.5, such as from about 7.0 to about 8.5, or from about 6.5 to about 8.0.

In other embodiments of a pharmaceutical composition of the invention, the pH of the composition is a pH selected from the list consisting of 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.8, 9.9, and 10.0. The pH of the composition may be at least 1 pH unit from (i.e., higher or lower than) the isoelectric point of the constituent compound of the invention, such as at least 2 pH units from (i.e., higher or lower than) the isoelectric point of the glucagon analogue compound of the invention.

In further embodiments of buffer-containing pharmaceutical compositions of the invention, the buffer or buffer substance is selected from the group consisting of: acetate buffers (e.g. sodium acetate), sodium carbonate, citrates (e.g. sodium citrate), glycylglycine, histidine, glycine, lysine, arginine, phosphates (e.g. chosen among sodium dihydrogen phosphate, disodium hydrogen phosphate and trisodium phosphate), TRIS (i.e., tris(hydroxymethyl)aminomethane), HEPES (i.e., 4-(2-hydroxyethyl)-1-piperazine-ethanesulfonic acid), BICINE (i.e., N,N-bis(2-hydroxyethyl)glycine), and TRICINE (i.e., N-[tris(hydroxymethyl)methyl]glycine), as well as succinate, malate, maleate, fumarate, tartrate, and aspartate buffers, and mixtures thereof.

In further embodiments of pharmaceutical compositions of the invention, the composition comprises a pharmaceutically acceptable preservative. Relevant preservatives include preservatives selected from the group consisting of: phenol, o-cresol, m-cresol, p-cresol, methyl p-hydroxybenzoate, ethyl p-hydroxybenzoate, propyl p-hydroxybenzoate, butyl p-hydroxybenzoate, 2-phenoxyethanol, 2-phenylethanol, benzyl alcohol, ethanol, chlorobutanol, thiomerosal, bronopol, benzoic acid, imidurea, chlorhexidine, sodium dehydroacetate, chlorocresol, benzethonium chloride, chlorphenesine [i.e. 3-(p-chlorphenoxy)propane-1,2-diol] and mixtures thereof. The preservative may be present in a concentration of from 0.1 mg/ml to 30 mg/ml, such as from 0.1 mg/ml to 20 mg/ml (e.g. from 0.1 mg/ml to 5 mg/ml, or from 5 mg/ml to 10 mg/ml, or from 10 mg/ml to 20 mg/ml) in the final liquid composition. The use of a preservative in pharmaceutical compositions is well known to the skilled worker. In this connection, reference may be made to Remington: *The Science and Practice of Pharmacy*, 19$^{th}$ edition, 1995.

In further embodiments, a pharmaceutical composition of the invention comprises an isotonicity agent (i.e., a pharmaceutically acceptable agent which is included in the composition for the purpose of rendering the composition isotonic). In some embodiments, the composition is administered to a subject by injection. Relevant isotonicity agents include agents selected from the group consisting of: salts (e.g., sodium chloride), sugars and sugar alcohols, amino acids (including glycine, arginine, lysine, isoleucine, aspartic acid, tryptophan and threonine), alditols (including glycerol, propyleneglycol (i.e. 1,2-propanediol), 1,3-propanediol and 1,3-butanediol), polyethylene glycols (including PEG400) and mixtures thereof. Suitable sugars include mono-, di- and polysaccharides, and water-soluble glucans, such as fructose, glucose, mannose, sorbose, xylose, maltose, lactose, sucrose, trehalose, dextran, pullulan, dextrin, cyclodextrin, soluble starch, hydroxyethyl starch and carboxymethylcellulose sodium salt. In some embodiments sucrose may be employed. Suitable sugar alcohols include hydroxylated $C_4$-$C_8$ hydrocarbons, including mannitol, sorbitol, inositol, galacititol, dulcitol, xylitol and arabitol. In some embodiments mannitol may be employed. The sugars or sugar alcohols mentioned above may be used individually or in combination. There is no fixed limit to the amount of isotonicity agent used, as long as it is soluble in the liquid formulation, establishes isotonicity and does not adversely effect the stability of the composition. The concentration of isotonicity agent (e.g. sugar or sugar alcohol) in the final liquid composition may be, e.g., from about 1 mg/ml to about 150 mg/ml, such as from 1 mg/ml to 50 mg/ml. In particular embodiments, the concentration may be from 1 mg/ml to 7 mg/ml, or from 8 mg/ml to 24 mg/ml, or from 25 mg/ml to 50 mg/ml. The use of an isotonicity agent in pharmaceutical compositions is well known to the skilled person. In this connection, reference may be made to Remington: *The Science and Practice of Pharmacy*, 19$^{th}$ edition, 1995.

In further embodiments of pharmaceutical compositions of the invention, the composition comprises a chelating agent. Relevant chelating agents include salts of ethylenediaminetetraacetic acid (EDTA), citric acid or aspartic acid, and mixtures thereof. The chelating agent may suitably be present in the final liquid composition in a concentration of from 0.1 mg/ml to 5 mg/ml, such as from 0.1 mg/ml to 2 mg/ml, or from 2 mg/ml to 5 mg/ml. The use of a chelating agent in pharmaceutical compositions is well-known to the skilled worker. In this connection, reference may be made to Remington: *The Science and Practice of Pharmacy*, 19$^{th}$ edition, 1995.

In further embodiments of pharmaceutical compositions of the invention, the composition comprises a stabilizer. The use of a stabilizer in pharmaceutical compositions is well-known to the skilled worker, and in this connection reference may be made to Remington: *The Science and Practice of Pharmacy*, 19$^{th}$ edition, 1995. Particularly useful pharmaceutical compositions of the invention are stabilized liquid compositions with therapeutically active components that include a compound of the invention (e.g., a peptide of the invention) that may otherwise possibly exhibit aggregate formation during storage in a liquid medium. In this context, "aggregate formation" refers to physical interactions between the peptide molecules that result in formation of larger assemblies that undergo some degree of visible precipitation from the solution. As used herein, "during storage in a liquid medium" refers to the storage of a liquid composition that, once prepared, is not necessarily immediately administered to a subject. Instead, following preparation, it may be packaged for storage, either in a liquid form, in a frozen state, or in a dried form for later reconstitution into a liquid form or other form suitable for administration to a subject. As used herein, "dried form" refers to an initially liquid pharmaceutical composition or formulation that has been dried by freeze-drying (i.e., lyophilization), by spray-drying or by air-drying. Aggregate formation by a peptide during storage of a liquid pharmaceutical composition thereof can adversely affect biological activity of the peptide in question, resulting in a loss of therapeutic efficacy of the pharmaceutical composition. Furthermore, aggregate formation may cause other problems, such as blockage of tubing, membranes, or pumps if such a peptide-containing pharmaceutical composition is administered using an infusion system. Thus, peptides of the invention may be beneficial in overcoming these problems.

Examples of stabilizers appropriate for incorporation in pharmaceutical compositions of the invention include, but are not limited to, the following: amino acids in their free base form or salt form, e.g. amino acids carrying a charged side chain, such as arginine, lysine, aspartic acid or glutamic acid, or amino acids such as glycine or methionine (in that incorporation of methionine may additionally inhibit oxidation of methionine residues in peptides comprising at least one methionine residue susceptible to such oxidation); certain polymers (e.g., polyethylene glycols (such as PEG 3350), polyvinylalcohol (PVA), polyvinylpyrrolidone (PVP), and carboxy-/hydroxycellulose and derivatives thereof); cyclodextrins; sulfur-containing substances (such as monothioglycerol, thioglycolic acid and 2-methylthioethanol); and surfactants (such as non-ionic surfactants, including non-ionic surfactants of the Poloxamer or Polysorbate (Tween) types. The use of a surfactant in pharmaceutical compositions is well known to the skilled worker. In this connection, reference may be made to Remington: *The Science and Practice of Pharmacy*, 19$^{th}$ edition, 1995.

Additional types of constituents may also be present in pharmaceutical compositions of the present invention. Non-limiting examples of classes of such constituents include wetting agents, emulsifiers, antioxidants, bulking agents, oleaginous vehicles and proteins (e.g., human serum albumin or gelatin).

Pharmaceutical compositions of the invention may be administered to a patient in need of such treatment at various sites, for example administration at sites which bypass absorption, such as in an artery or vein or in the heart, and at sites which involve absorption, such as in the skin, under the skin, in a muscle or in the abdomen. More generally, administration of pharmaceutical compositions according to the invention may be by a variety of routes of administration, such as or example parenteral, epidermal, dermal or transdermal routes. In some embodiments, other routes such as lingual, sublingual, buccal, oral, vaginal or rectal may be useful.

Compositions of the invention may be administered in various dosage forms, for example solutions, suspensions or emulsions, and are useful in the formulation of controlled-, sustained-, protracted-, retarded- or slow-release drug delivery systems. More specifically, but not exclusively, pharmaceutical compositions of the invention are useful in connection with parenteral controlled-release and sustained-release systems, well known to those skilled in the art. General reference may be made in this connection to *Handbook of Pharmaceutical Controlled Release* (Wise, D. L., ed., Marcel Dekker, New York, 2000) and *Drugs and the Pharmaceutical Sciences* vol. 99: *Protein Formulation and Delivery* (MacNally, E. J., ed., Marcel Dekker, New York, 2000).

Parenteral administration (of a liquid pharmaceutical composition of the invention) may be performed, for example, by subcutaneous, intramuscular, intraperitoneal or intravenous injection by means of a syringe, suitably a pen-like syringe. Alternatively, parenteral administration can take place by means of an infusion pump, e.g. in the form of a device or system borne by a subject or patient and comprising a reservoir containing a liquid composition of the invention and an infusion pump for delivery/administration of the composition to the subject or patient, or in the form of a corresponding miniaturized device suitable for implantation within the body of the subject or patient.

The term "stabilized composition" as employed herein refers to a composition having increased physical stability, increased chemical stability or increased physical and chemical stability. The term "physical stability" as used herein refers to a measure of the tendency of a peptide (e.g., a compound of the invention) to form soluble or insoluble aggregates of the peptide, for example as a result of exposure of the peptide to stresses and/or interaction with interfaces and surfaces that are destabilizing, such as hydrophobic surfaces and interfaces. Physical stability of aqueous peptide compositions may be evaluated by means of visual inspection and/or turbidity measurements after exposing the composition, filled in suitable containers (e.g. cartridges or vials), to mechanical/physical stress (e.g. agitation) at different temperatures for various time periods. A composition may be classified as physically unstable with respect to peptide aggregation when it exhibits visual turbidity. Alternatively, the turbidity of a composition can be evaluated by simple turbidity measurements well-known to the skilled person. Physical stability of an aqueous peptide composition can also be evaluated by using an agent that functions as a spectroscopic probe of the conformational status of the peptide. The probe is preferably a small molecule that preferentially binds to a non-native conformer of the peptide. One example of such a small-molecular spectroscopic probe is Thioflavin T, which is a fluorescent dye that has been widely used for the detection of amyloid fibrils. In the presence of fibrils, and perhaps also other peptide configurations, Thioflavin T gives rise to a new excitation maximum at about 450 nm and enhanced emission at about 482 nm when bound to a fibril form of a peptide. Unbound Thioflavin T is essentially non-fluorescent at the wavelengths in question.

The term "chemical stability" as used herein refers to stability of a peptide with respect to covalent chemical changes in the peptide structure that lead to formation of chemical degradation products with potentially lower biological potency and/or potentially increased immunogenicity compared to the native peptide structure. Various chemical degradation products can be formed, depending on the type and detailed nature of the native peptide and the environment to which the peptide is exposed. In practise, elimination of chemical degradation in peptide compositions in general cannot be avoided completely, and the formation of increasing amounts of chemical degradation products is often seen during storage and use of such compositions, as is well-known to the person skilled in the art. Many peptides are susceptible to a degradation process in which the side-chain amide group in glutaminyl or asparaginyl residues is hydrolysed to form a free carboxylic acid. Other degradation pathways involve formation of high-molecular-weight transformation products in which two or more peptide molecules become covalently bound to each other through transamidation and/or disulfide interactions, leading to formation of covalently bound oligomer and polymer degradation products (see, e.g., *Stability of Protein Pharmaceuticals*, Ahern. T. J. and Manning M. C., Plenum Press, New York 1992). Oxidation (e.g., of methionine residues) is another form of chemical degradation of peptides. The chemical stability of a peptide composition may be evaluated by measuring the amounts of chemical degradation products at various time-points after exposure to different environmental conditions (for example, formation of degradation products may often be accelerated by increasing temperature). The amount of each individual degradation product may be determined by separation of the degradation products on the basis of molecular size and/or charge using various chromatographic techniques (e.g. SEC-HPLC and/or RP-HPLC).

The chemical instability of glucagon per se at low pH is mainly due to isomerisation and cleavage of aspartic acid residues, deamidation of glutamine residues and oxidation of methionine. Generally speaking, Asn and Gln deamidation occurs at high pH, with significant rates at physiological pH around pH 7.4 via a cyclic imide ring intermediate which can open to create L-Asp and L-isoAsp or L-Glu and L-isoGlu, respectively. The cyclic imide ring intermediate also may lead to the formation of small amounts of the corresponding D-isomers, indicating a slow racemisation of the cyclic imide.

At pH values below physiological pH, the rate of deamidation of Asn and Gln is reduced, but the rate of formation of a cyclic imide from Asp and Glu, and hence isomerisation, increases with decreasing pH. Cyclic imide formation is greatest between pH 4 and pH 6. Formation of the cyclic imide intermediate can also result in cleavage of the peptide sequence.

As outlined above, a "stabilized composition" may thus refer to a composition with increased physical stability, or increased chemical stability, or increased physical and chemical stability. In general, a composition should be stable during use and storage (in compliance with recommended use and storage conditions) at least until the specified expiration date is reached.

In certain embodiments of pharmaceutical compositions of the invention (e.g., liquid compositions) the composition is stable for at least 2 weeks of usage and for at least 6 months of storage. In further embodiments, the composition is stable for at least 2 weeks of usage and for at least one year of storage. In still further embodiments, the composition is stable for at least 2 weeks of usage and for at least two years of storage. In other embodiments, the composition is stable for at least 4 weeks of usage and for at least two years of storage, or even for at least 4 weeks of usage and for more than 3 years of storage. Particularly useful embodiments of such pharmaceutical compositions of the invention are stable for at least 6 weeks of usage and for at least 3 years of storage. In this regard, the term "usage" for the purposes of this paragraph refers to taking the pharmaceutical composition out of storage for the purpose of employing the composition for therapeutic purposes, and thereby subjecting it to varying ambient conditions (conditions of light, dark, temperature, agitation etc.), whilst the term "storage" for the purposes of this paragraph refers to storage under non-agitated conditions in a refrigerator or freezer at a temperature not exceeding about 5° C. The skilled worker will understand the typical range of usage and storage conditions that these pharmaceutical compositions may be subjected to.

Nucleic Acids, Expression Vectors and Host Cells

The invention provides a nucleic acid molecule (e.g. an isolated nucleic acid molecule) encoding a compound of the invention, or the peptide sequence Z of a compound of the invention.

It will be understood that a compound of the invention, or peptide sequence Z, can typically only be encoded by a nucleic acid sequence when the peptide sequence Z comprises only naturally occurring amino acids, i.e. the twenty amino acids which occur naturally in mammalian proteins.

As discussed above, the invention relates, inter alia, to an expression vector comprising a nucleic acid construct sequence of the invention, optionally in combination with one or more sequences to direct its expression, and to a host cell containing an expression vector of the invention. Preferably the host cell is capable of expressing and secreting a compound of the invention or a compound having the peptide sequence Z of a compound of the invention. In some embodiments, the present invention provides a method of producing a compound of the invention, wherein the method comprises culturing host cells of the invention under conditions suitable for expressing the compound and purifying the compound thus produced.

Alternatively, the method may comprise expressing a compound having the peptide sequence Z of a compound of the invention, and subsequently modifying the N- and/or C-terminus to obtain a compound of the invention. The invention further provides (i) a nucleic acid of the invention, (ii) an expression vector of the invention, and (iii) a host cell capable of expressing and optionally secreting a compound of the invention, for use in a method of medical treatment. The nucleic acid, expression vector and host cells may be used for treatment of any of the disorders described herein which may be treated with a compound of the invention themselves. References to a pharmaceutical composition comprising a compound of the invention, administration of a compound of the invention, or any therapeutic use thereof, should therefore be construed to encompass the equivalent use of a nucleic acid, expression vector or host cell of the invention, except where the context demands otherwise.

Peptide Synthesis

Peptides of the present invention may be manufactured by standard chemical synthetic methods, or by using recombinant expression systems, or by any other suitable state-of-the-art method. Thus, the glucagon analogues may be synthesized in a number of ways, including, inter alia, methods comprising:

(a) synthesizing the peptide by means of solid-phase or liquid-phase methodology, either stepwise or by fragment assembly, and isolating and purifying the final peptide product; or (b) expressing a nucleic acid construct that encodes the peptide in a host cell, and recovering the expression product from the host cell culture; or (c) effecting cell-free in vitro expression of a nucleic acid construct that encodes the peptide, and recovering the expression product;

or employing any combination of methods as in (a), (b) and (c) to obtain fragments of the peptide, subsequently joining (e.g., ligating) the fragments to obtain the complete peptide, and recovering the peptide.

It may be preferable to synthesize compounds of the invention by means of solid-phase or liquid-phase peptide synthesis, the methodology of which is well known to persons of ordinary skill in the art of peptide synthesis. Reference may also be made in this respect to, for example, WO 98/11125 and Fields, G. B. et al., 2002, *"Principles and practice of solid-phase peptide synthesis"*. In: *Synthetic Peptides* (2nd Edition), and examples provided therein.

For recombinant expression, nucleic acid constructs of the invention may be inserted in suitable vectors to form cloning or expression vectors carrying the nucleic acid constructs of the invention (such vectors also constituting aspects of the present invention). The vectors can, depending on purpose and type of application, be in the form of plasmids, phages, cosmids, mini-chromosomes, or viral, but naked DNA which is only expressed transiently in certain cells may also be an important vector. Preferred cloning and expression vectors (plasmid vectors) of the invention are capable of replication, thereby enabling high copy-numbers for the purposes of high-level expression or high-level replication for subsequent cloning.

In general, an expression vector may comprise the following features in the 5'3' direction and operably linked: a promoter for driving expression of the nucleic acid fragment of the invention, optionally a nucleic acid sequence encoding a leader peptide enabling secretion (to the extracellular phase or, where applicable, into the periplasma), the nucleic acid fragment encoding the peptide of the invention, and optionally a nucleic acid sequence encoding a terminator. The expression vector also may comprise additional features such as selectable markers and origins of replication. When operating with expression vectors in producer strains or cell lines, it may be preferred that the vector is capable of integrating into the host cell genome. The skilled person will be familiar with suitable vectors, and will be able to design one according to the specific requirements in question.

Vectors of the invention may be used to transform host cells to produce compounds of the invention. Such transformed cells, which also constitute embodiments of the invention, can be cultured cells or cell lines used for propagation of the nucleic acid fragments and vectors of the invention, or may be used for recombinant production of the peptides of the invention.

In some embodiments, the transformed cells of the invention are micro-organisms such as bacteria (e.g., species of *Escherichia* (e.g., *E. coli*), *Bacillus* (e.g., *B. subtilis*), *Salmonella* or *Mycobacterium* (preferably non-pathogenic, e.g., *M. bovis* BCG)), yeasts (e.g., *Saccharomyces cerevisiae* or *Pichia pastoris*), or protozoans. Alternatively, the transformed cells may be derived from a multicellular organism, e.g., the cells may be fungal cells, insect cells, algal cells, plant cells, or animal cells such as mammalian cells. For the purposes of cloning and/or optimised expression, the transformed cell may be capable of replicating the nucleic acid construct of the invention. Cells expressing the nucleic acid constructs are useful embodiments of the invention, and may be used for small-scale or large-scale preparation of peptides of the invention.

When producing a peptide of the invention by means of transformed cells, it will be convenient, although not essential, that the expression product is secreted into the culture medium.

Efficacy

The compounds of the invention have glucagon agonist activity.

Binding of the relevant compounds to glucagon (Glu or GCG) receptors may be used as an indication of agonist activity. In alternative embodiments, a biological assay which measures intracellular signalling caused by binding of the compound to the receptor may also be used. For example, activation of the glucagon receptor by a glucagon receptor agonist will stimulate cellular cyclic AMP (cAMP) formation. Thus, production of cAMP in suitable cells expressing the receptor can be used to monitor receptor activity.

The skilled person will be aware of suitable assay formats, and examples are provided below. By way of example, the assay may employ the human glucagon receptor (GCG-R) having primary accession number GI:4503947 (NP 000151.1) or having primary accession number P47871. The skilled worker will understand in this connection that when sequences of precursor proteins are referred to, assays may make use of the mature protein lacking the signal sequence. Suitable cells are typically mammalian cells, e.g. rodent or primate cells, e.g. rat, mouse or hamster cells, or human cells such as HEK293 cells. They may express their endogenous glucagon receptor or may have been engineered to express glucagon receptor (e.g. having the human sequence referred to above). The assay may be performed using the materials and under the conditions set out in Example 3.

$EC_{50}$ values may be used as a numerical measure of agonist potency at a given receptor, the $EC_{50}$ value being a measure of the concentration of a compound required to achieve half of that compound's maximal activity towards the receptor in question in a particular assay.

Therapeutic Uses

Compounds (and pharmaceutically acceptable salts or solvates thereof) of the invention, as well as pharmaceutical compositions of the invention, may be useful in the treatment or prevention of a variety of conditions or disorders. Optionally, the compounds (and pharmaceutically acceptable salts or solvates thereof) may be used in combination with one or more additional therapeutically active substances. Relevant therapeutic uses thus include: treatment or prevention of hypoglycaemia (both acute and chronic), type 2 diabetes (including disease progression in type 2 diabetes), impaired glucose tolerance, type 1 diabetes, obesity (including diseases or states related to overweight or obesity), coronary heart disease, atherosclerosis, hypertension, dyslipidemia, hepatic steatosis, β-blocker poisoning, insulinoma and Von Gierkes disease; preventing a subject from becoming overweight; reducing body weight; decreasing food intake; increasing energy expenditure; delaying progression from impaired glucose tolerance (IGT) to type 2 diabetes; delaying progression from type 2 diabetes to insulin-requiring diabetes; regulating appetite or inducing satiety (including treatment of bulimia and treatment of binge-eating); and preventing weight regain after successful weight loss. As a general principle, compounds (and pharmaceutically acceptable salts or solvates thereof) of the invention, as well as pharmaceutical compositions of the invention, may be useful to control blood glucose levels.

Among forms of hypoglycaemia capable of treatment or prevention in accordance with the invention are diabetic hypoglycaemia (including acute insulin-induced hypoglycaemia), non-diabetic hypoglycaemia, reactive hypoglycaemia, fasting hypoglycaemia, drug-induced hypoglycaemia, alcohol-induced hypoglycaemia, gastric bypass-induced hypoglycaemia, and hypoglycaemia occurring during pregnancy.

Additional applications of compounds (and pharmaceutically acceptable salts or solvates thereof) of the invention, and pharmaceutical compositions of the invention, include uses as a smooth-muscle relaxant (spasmolytic agent) in connection with imaging procedures (e.g., X-ray, computer tomography (CT) or magnetic resonance (MR) imaging), such as imaging of the abdominal region.

Combination Therapy

As already indicated above, treatment with a compound (or pharmaceutically acceptable salt or solvate thereof) according to the present invention may take place in combination with one or more other pharmacologically active substances or agents, e.g., selected from antidiabetic agents, antiobesity agents, appetite-regulating agents, antihypertensive agents, agents for the treatment and/or prevention of complications resulting from or associated with diabetes, and agents for the treatment and/or prevention of complications and disorders resulting from or associated with obesity. In the present context, the expression "antidiabetic agent" includes compounds for the treatment and/or prophylaxis of insulin resistance and diseases wherein insulin resistance is the pathophysiological mechanism.

Examples of such pharmacologically active substances are insulin and insulin analogues, GLP-1 agonists, sulfonylureas (e.g. tolbutamide, glibenclamide, glipizide and gliclazide), biguanides (e.g. metformin), meglitinides, glucosidase inhibitors (e.g. acarbose), glucagon antagonists, dipeptidyl peptidase IV (DPP-IV) inhibitors, inhibitors of hepatic enzymes involved in stimulation of gluconeogenesis and/or glycogenolysis, glucose uptake modulators, thiazolidinediones such as troglitazone and ciglitazone, compounds modifying the lipid metabolism such as antihyperlipidemic agents (e.g. HMG CoA inhibitors (statins)), compounds lowering food intake, RXR agonists and agents acting on the ATP-dependent potassium channel of the β-cells, e.g. glibenclamide, glipizide, gliclazide and repaglinide; cholestyramine, colestipol, clofibrate, gemfibrozil, lovastatin, pravastatin, simvastatin, probucol, dextrothyroxine, neteglinide, repaglinide; β-blockers, such as alprenolol, atenolol, timolol, pindolol, propranolol and metoprolol, ACE (angiotensin converting enzyme) inhibitors such as benazepril, captopril, enalapril, fosinopril, lisinopril, alatriopril, quinapril and ramipril, calcium channel blockers, such as nifedipine, felodipine, nicardipine, isradipine, nimodipine, diltiazem and verapamil, and α-blockers, such as doxazosin, urapidil, prazosin and terazosin; CART (cocaine amphetamine regulated transcript) agonists, NPY (neuropeptide Y) antagonists, MC4 (melanocortin 4) agonists, orexin antagonists, TNF (tumor necrosis factor) agonists, CRF (corticotropin releasing factor) agonists, CRF BP (corticotropin releasing factor binding protein) antagonists, urocortin agonists, β3 agonists, MSH (melanocyte-stimulating hormone) agonists, MCH (melanocyte-concentrating hormone) antagonists, CCK (cholecystokinin) agonists, serotonin re-uptake inhibitors, serotonin and noradrenaline reuptake inhibitors, mixed serotonin and noradrenergic compounds, 5HT (serotonin) agonists, bombesin agonists, galanin antagonists, growth hormone, growth hormone releasing compounds, TRH (thyrotropin releasing hormone) agonists, UCP 2 or 3 (uncoupling protein 2 or 3) modulators, leptin agonists, DA agonists (e.g. bromocryptin, doprexin), lipase/amylase inhibitors, RXR (retinoid X receptor) modulators, TR β agonists, and histamine H3 antagonists.

Any suitable combination of a compound or compounds according to the invention with one or more of the above-mentioned compounds, and optionally one or more further pharmacologically active substances, is within the scope of the present invention.

Experimental Methods

Abbreviations employed in the following are as follows:
COMU: 1-[(1-(cyano-2-ethoxy-2-oxoethylideneaminooxy)-dimethylamino-morpholinomethylene)]methanaminium hexafluorophosphate
DCM: dichloromethane
DMF: N,N-dimethylformamide
DIPEA: diisopropylethylamine
EtOH: ethanol
Et$_2$O: diethyl ether
HATU: N-[(dimethylamino)-1H-1,2,3-triazol[4,5-b]pyridine-1-ylmethylene]-N-methylmethanaminium hexafluorophosphate N-oxide
HPLC: high-performance liquid chromatography
IBMX: 3-isobutyl-1-methylxanthine
MeCN: acetonitrile
MS: mass spectroscopy
PBS phosphate-buffered saline
RP: reverse phase
TFA: trifluoroacetic acid
TIS: triisopropylsilane General Synthesis Procedure for Glucagon Analogues Solid phase peptide synthesis (SPPS) was performed on a microwave assisted synthesizer using standard Fmoc strategy in DMF on a polystyrene resin (TentaGel S Ram or Tentagel S PHB-Thr(tBu)). HATU or COMU was used as coupling reagent together with DIPEA as base. Piperidine (20% in DMF) was used for deprotection. Pseudoprolines: Fmoc-Phe-Thr(Ψ Me, Me pro)-OH, Fmoc-Asp-Ser(Ψ, Me, Me pro)-OH and Fmoc-Glu-Ser(Ψ, Me, Me pro)-OH (purchased from NovaBiochem) were used where applicable. Human glucagon was likewise synthesized and purified using synthesis methodology and purification procedures as described herein.

Cleavage:

The crude peptide was cleaved from the resin by treatment with 95/2.5/2.5% (v/v) TFA/TIS/water at room temperature for 2 h. Most of the TFA was removed at reduced pressure, and the crude peptide was precipitated and washed with diethyl ether and allowed to dry at ambient temperature.

Peptide Purification

The crude peptides were purified by standard RP HPLC with a gradient of buffer A (0.1% aqueous TFA) and buffer B (aqueous solution containing 0.1% TFA and 90% MeCN). Fractions were analysed by analytical HPLC and MS, and relevant fractions were pooled and lyophilised.

The peptides were further purified by preparative RP HPLC using a gradient of buffer A' (0.1% aqueous formic acid) and buffer B' (aqueous solution containing 0.1% formic acid and 90% MeCN). TFA was added to the collected fractions prior to lyophilisation. The final product was characterised by analytical HPLC and MS.

Analytical HPLC Method

The peptides were analyzed by an analytical HPLC method using a gradient of buffer A' (see above) and buffer B' (see above).

EXAMPLE 1

Synthesis of Compound 7

Compound 7 (SEQ ID NO: 8) was synthesized on a CEM Liberty Peptide Synthesizer using Tentagel S PHB-Thr(tBu) resin (1.13 g, 0.24 mmol/g), COMU as coupling reagent, DMF as the solvent, and Fmoc-chemistry as described above. Pseudoprolines Fmoc-Phe-Thr(Ψ Me, Me pro)-OH (in position 6/7) and Fmoc-Glu-Ser(Ψ, Me, Me pro)-OH (in position 15/16) were used in the sequence.

The peptide was cleaved from the resin as described above, and the purification was performed on a Gemini-NX column (5 cm, C18, 10 micron) with a 35 ml/min flow of a mixture of buffer A (see above) and buffer B (see above). The product was eluted with a linear gradient of 20-50% buffer B over 47 min, and relevant fractions were analyzed by analytical HPLC and MS. Pooled fractions were lyophilized and redissolved in water prior to further purification on a Gemini-NX column (2.12×25 cm, C18 (110A); 10 micron) with a 10 ml/min flow of a mixture of buffer A' (see above) and buffer B' (see above). The product was eluted with a linear gradient of 5-40% buffer B' over 47 min, and relevant fractions were analyzed by analytical HPLC and MS. TFA was added to the pooled fractions and they were lyophilized to give 112 mg. The purity was 99% as determined by analytical HPLC (see above), and the monoisotopic mass was 3409.55 Da as determined by MS (calc. 3409.58 Da).

EXAMPLE 2

Generation of Cell Line Expressing Human Glucagon Receptor

The cDNA encoding the human glucagon receptor (Glucagon-R) (primary accession number P47871) was cloned from the cDNA clone BC104854 (MGC:132514/IMAGE:8143857). The DNA encoding the Glucagon-R was amplified by PCR using primers encoding terminal restriction sites for subcloning. The 5'-end primers additionally encoded a near-Kozak consensus sequence to ensure efficient translation. The fidelity of the DNA encoding the Glucagon-R was confirmed by DNA sequencing. The PCR products encoding the Glucagon-R were subcloned into a mammalian expression vector containing a neomycin (G418) resistance marker. The mammalian expression vector encoding the Glucagon-R was transfected into HEK293 cells by a standard calcium phosphate transfection method. 48 hr after transfection, cells were seeded for limited dilution cloning and selected with 1 mg/ml G418 in the culture medium. Three weeks later twelve surviving colonies of Glucagon-R-expressing cells were picked, propagated and tested in the Glucagon-R efficacy assay as described below. One Glucagon-R expressing clone was chosen for compound profiling.

EXAMPLE 3

Glucagon Receptor Assay

HEK293 cells expressing the human Glucagon-R were seeded at 60,000 cells per well in 96-well microtiter plates coated with 0.01% poly-L-lysine, and grown for 1 day in culture in 100 µl growth medium. For analyses of the induction of cAMP by the Glucagon-R we used the AlphaScreen® cAMP Assay Kit from Perkin Elmer, according to manufacturer instructions. On the day of analysis, growth medium was removed and the cells were washed once with 200 ml of the included Assay buffer with IBMX. Cells were incubated in 100 ml Assay buffer/IBMX containing increasing concentrations of test peptides for 15 min at 37° C. Then the peptides/Assay buffer was removed and cells were lysed by addition of 80 ml Lysis buffer pr. well and incubation for at least 10 min at room temperature. From each well 10 ml cell lysate was transferred to a 384-well OptiPlate and mixed with Donor and Acceptor beads and incubated for 1 h at room temperature. The cAMP content was measured on an Envision plate reader. $EC_{50}$ and relative efficacies compared to reference compound (glucagon) were estimated by computer-aided curve fitting.

EXAMPLE 4

Solubility Assessment

A stock solution of the test peptide (2 mg/ml; determined by measurement of the absorption of the solution at 280 nm, and using the theoretical extension coefficient based on the content of tryptophan and tyrosine in the peptide) in demineralized water adjusted to pH 2.5 with HCl was prepared, and aliquots were diluted 1:1 in 100 mM acetate buffer (pH 4.0) and 100 mM phosphate buffer (pH 7.5), respectively, and loaded in a standard flat-bottom, non-sterile 96-well UV Microplate. The absorbance of samples (single samples, n=1) at 280 and 325 nm was measured in an absorbance-based plate reader, which was preheated to ambient temperature. The turbidity absorbance criterion for a peptide solubility of ≥1 mg/ml was an absorbance at 325 nm≤0.02 absorbance units (which is 5 to 6 times the standard deviation of 8 buffer samples in a plate).

Numerous compounds of the invention exhibit a solubility of ≥1 mg/ml in the pH range from 4 to 7.5, more specifically at pH 4 and pH 5 (e.g. in acetate buffer), and at pH 6, pH 7 and pH 7.5 (e.g. in phosphate buffer).

EXAMPLE 5

Assessment of Physical Stability

Aggregation in the form of fibril formation was detected using the amyloid-specific dye Thioflavin T (ThT), which is frequently employed to demonstrate the presence of fibrils in solution (see, e.g., Groenning, M., *J. Chem. Biol.* 3(1) (2010), pp. 1-18; Groenning et al., *J. Struct. Biol.* 158 (2007) pp. 358-369; and Levine, H., III, *Protein Sci.* 2 (1993) pp. 404-410) All test peptides were dissolved in demineralized water adjusted to pH 2.5 with HCl, at ambient temperature. A solution containing 1 mg/ml of peptide, 40 µM ThT and 50 mM phosphate buffer, pH 7.5, was loaded in a 96-well black fluorescence plate (clear bottom) in triplicate. Data were collected at fixed intervals of 10 min, each preceded by 300 s of automixing (agitation), over a period of 96 hours at 40° C. The entire experiment was repeated, but without agitation. Physical stability, expressed as lag-time of fibril formation (in hours), was defined as the intersection between two linear regressions representing the initial stable phase and the growth phase.

EXAMPLE 6

Chemical Stability Assessment

Stock solutions of each test peptide (1 mg/ml; determined by measurement of the absorption of the solution at 280 nm, and using the theoretical extension coefficient based on the content of tryptophan and tyrosine in the peptide) in 50 mM acetate buffer (pH 4.0) and in 50 mM phosphate buffer (pH 7.5), respectively, were prepared. Samples were placed in glass vials and incubated at 40° C. The samples were analysed by reverse-phase HPLC on a C18 column with gradient elution using an acetonitrile/trifluoroacetic acid/water eluent system. The area-percentage (area-%) of the main peak after incubation time T=t (relative to time T=0) was detected by UV spectrometry at 220 nm.

The purity was first determined as follows:

Purity(area-%)=(area of main peak/total area of all peaks)×100.

The purity was then normalized between time points by setting purity at time 0 (T=0) to 100 for each pH value for a given peptide, as follows:

Normalised area-% at time $t(T=t)$=[area-% $(T=t)$/area-% $(T=0)$]×100.

The in vitro activity results (expressed as $EC_{50}$ values) and the results of the assessment of solubility are summarized in Table 1 (below), and the physical and chemical stability assessment results are summarized in Table 2 (below). Normalized purity values in Table 2 were determined after 14 days of incubation.

EXAMPLE 7

Acute Glucose Release

The effect of Compound 14 of the invention (doses of 20 and 60 nmol/kg body weight, respectively) on acute glucose release in euglycemic male Sprague-Dawley rats (Taconic, Lille Skensved, Denmark, 9-10 weeks old) in comparison with that of native human glucagon (dose 20 nmol/kg) was investigated. The rats were fasted for 5 hours prior to dosing. The animals (n=6/group) were injected once subcutaneously (SC) with vehicle (PBS, pH 7.4), test compound or glucagon. Blood samples were collected from the tail vein prior to dosing (t=0) and every 15 minutes for 2 hours thereafter using 5 μl capillary tubes. Animals were anaesthetized (with a standard mixture of hypnorm/dormicum) during the experiment to ensure stable baseline blood glucose levels. Blood glucose concentrations were determined using a Biosen Glucose Analyser (EKF-diagnostic GmbH, Germany). The data are summarized in FIG. 1.

EXAMPLE 8

Pharmacokinetics

A comparative pharmacokinetic evaluation of native human glucagon and a representative compound of the present invention in mice, rats and dogs was made. The two compounds exhibited similar pharmacokinetic characteristics, e.g. with respect to half-life ($t_{1/2}$) and volume of distribution.

TABLE 1

EC$_{50}$ and solubility data for compounds of the invention

| Compound No. | Seq. ID No. | GCG-R EC$_{50}$ in vitro [nM]# | Solubility pH 7.5 |
|---|---|---|---|
| Glucagon | 1 | 0.013 | <1 mg/mL |
| 1 | 2 | 0.064 | ≥1 mg/mL |
| 2 | 3 | 0.18 | ≥1 mg/mL |
| 3 | 4 | 0.030 | ≥1 mg/mL |
| 4 | 5 | 0.34 | ≥1 mg/mL |
| 5 | 6 | 0.17 | ≥1 mg/mL |
| 6 | 7 | 1.0 | ≥1 mg/mL |
| 7 | 8 | 0.93 | ≥1 mg/mL |

TABLE 1-continued

EC$_{50}$ and solubility data for compounds of the invention

| Compound No. | Seq. ID No. | GCG-R EC$_{50}$ in vitro [nM]# | Solubility pH 7.5 |
|---|---|---|---|
| 8 | 9 | 0.38 | ≥1 mg/mL |
| 9 | 10 | 0.030 | ≥1 mg/mL |
| 10 | 11 | 0.32 | ≥1 mg/mL |
| 11 | 12 | 0.11 | ≥1 mg/mL |
| 12 | 13 | 0.030 | ≥1 mg/mL |
| 13 | 14 | 0.070 | ≥1 mg/mL |
| 14 | 15 | 0.15 | ≥1 mg/mL |
| 15 | 16 | 0.030 | ≥1 mg/mL |
| 16 | 17 | 0.39 | ≥1 mg/mL |
| 17 | 18 | 0.029 | ≥1 mg/mL |
| 18 | 19 | 0.026 | ≥1 mg/mL |
| 19 | 20 | 0.054 | ≥1 mg/mL |
| 20 | 21 | 0.24 | ≥1 mg/mL |
| 21 | 22 | 0.0095 | ≥1 mg/mL |
| 22 | 23 | 0.024 | ≥1 mg/mL |
| 23 | 24 | 0.16 | ≥1 mg/mL |
| 24 | 25 | 0.0078 | ≥1 mg/mL |
| 25 | 26 | 0.0066 | ≥1 mg/mL |
| 26 | 27 | 0.0069 | ≥1 mg/mL |
| 27 | 28 | 0.063 | ≥1 mg/mL |
| 28 | 29 | 0.035 | ≥1 mg/mL |
| 29 | 30 | 0.023 | ≥1 mg/mL |
| 30 | 31 | 0.016 | ≥1 mg/mL |
| 31 | 32 | 0.0072 | ≥1 mg/mL |
| 32 | 33 | 0.0093 | ≥1 mg/mL |
| 33 | 34 | 0.044 | ≥1 mg/mL |
| 34 | 35 | 0.028 | ≥1 mg/mL |
| 35 | 36 | 0.014 | ≥1 mg/mL |
| 36 | 37 | 0.010 | ≥1 mg/mL |
| 37 | 38 | 0.094 | ≥1 mg/mL |
| 38 | 39 | 0.0047 | ≥1 mg/mL |
| 39 | 40 | 0.0044 | ≥1 mg/mL |
| 40 | 40 | 0.0035 | ≥1 mg/mL |
| 41 | 41 | 0.0038 | ≥1 mg/mL |

All values quoted to two significant figures

TABLE 2

Physical and chemical stability data for compounds of the invention.

| Compound No. | Seq. ID No: | Normalized purity pH 4.0 after 14 days [%] | Normalized purity pH 7.5 after 14 days [%] | Physical Stability at pH 7.5 [hrs:mins] (non-agitated) | Physical Stability at pH 7.5 [hrs:mins] (agitated) |
|---|---|---|---|---|---|
| 1 | 2 | N/A | N/A | 05:18 ± 00:23 | 01:49 ± 00:10 |
| 2 | 3 | 83.5 | 86.2 | FND | FND |
| 3 | 4 | 85.0 | 86.5 | FND | 72:50 ± 06:16 |
| 4 | 5 | 80.5 | 84.6 | FND | FND |
| 5 | 6 | 91.8 | 89.6 | FND | FND |
| 8 | 9 | Not performed | Not performed | 85 | 57:02 ± 0:43 |
| 9 | 10 | Not performed | Not performed | onset | 53:20 ± 05:46 |
| 10 | 11 | Not performed | Not performed | FND | FND |
| 11 | 12 | 78.6 | 89.9 | FND | FND |
| 12 | 13 | 86.8 | 90.8 | FND | FND |
| 13 | 14 | 84.6 | 88.8 | FND | 80:10 ± 14:54 |
| 14 | 15 | 89.5 | 92.4 | FND | FND |
| 15 | 16 | 89.1 | 95.1 | FND | FND |
| 16 | 17 | 89.1 | Not performed | 12:57 ± 00:02 | Not performed |
| 17 | 18 | 89.9 | 88.3 | 62 ± 4 | 41:33 ± 04:18 |
| 18 | 19 | Not performed | Not performed | 15:04 ± 00:41 | 03:48 ± 00:06 |
| 19 | 20 | Not performed | Not performed | onset | Not performed |
| 20 | 21 | Not performed | Not performed | FND | FND |
| 21 | 22 | 89.8 | 93.5 | FND | FND |
| 22 | 23 | 91.1 | 95.3 | FND | FND |
| 23 | 24 | Not performed | Not performed | FND | FND |
| 24 | 25 | 92.8 | 94.4 | FND | FND |
| 25 | 26 | 93.8 | 89.8 | FND | FND |
| 26 | 27 | 90 | 93.9 | FND | FND |
| 27 | 28 | Not performed | Not performed | 46:20 ± 04:43 | 18:00 ± 04:00 |
| 28 | 29 | Not performed | Not performed | 08:33 ± 00:05 | 02:20 ± 00:17 |
| 29 | 30 | 91 | 91.6 | FND | FND |

TABLE 2-continued

Physical and chemical stability data for compounds of the invention.

| Compound No. | Seq. ID No: | Normalized purity pH 4.0 after 14 days [%] | Normalized purity pH 7.5 after 14 days [%] | Physical Stability at pH 7.5 [hrs:mins] (non-agitated) | Physical Stability at pH 7.5 [hrs:mins] (agitated) |
|---|---|---|---|---|---|
| 30 | 31 | 88.6 | 91.4 | FND | FND |
| 31 | 32 | 93.1 | 91.7 | FND | FND |
| 32 | 33 | 91.2 | 96.3 | FND | FND |
| 33 | 34 | Not performed | Not performed | Not performed | FND |
| 34 | 35 | Not performed | Not performed | Not performed | FND |
| 35 | 36 | Not performed | Not performed | Not performed | FND |
| 36 | 37 | Not performed | Not performed | Not performed | FND |
| 37 | 38 | Not performed | Not performed | Not performed | FND |
| 38 | 39 | Not performed | Not performed | Not performed | FND |

*FND = fibrillation not detected

The invention claimed is:

1. The compound:
Hy-HSQGTFTSDYSKYLD-Aib-ARAEEFVKWLEST-OH (SEQ ID NO: 22)
or a pharmaceutically acceptable salt thereof.

2. A pharmaceutical composition comprising a compound, or a pharmaceutically acceptable salt thereof, according to claim 1 and a pharmaceutically acceptable carrier.

* * * * *

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 10,442,847 |
| (45) | ISSUED | : | October 15, 2019 |
| (75) | INVENTOR | : | Ditte Riber et al. |
| (73) | PATENT OWNER | : | Zealand Pharma A/S |
| (95) | PRODUCT | : | ZEGALOGUE® (dasiglucagon) |

This is to certify that an application under 35 U.S.C. § 156 has been filed in the United States Patent and Trademark Office, requesting extension of the term of U.S. Patent No. 10,442,847 based upon the regulatory review of the product ZEGALOGUE® (dasiglucagon) by the Food and Drug Administration. According to United States Patent and Trademark Office records, the original expiration date of the patent as of the date of issuance of this certificate is February 3, 2035. Because it appears that the requirements of the law have been met, this certificate extends the term of the patent for the period of

(94)  47 days subject to the payment of maintenance fees as provided by law, with all rights pertaining thereto as provided by 35 U.S.C. § 156.

I have caused the seal of the United States Patent and Trademark Office to be affixed this 18th day of November 2025.

John A. Squires
Under Secretary of Commerce for Intellectual Property and
Director of the United States Patent and Trademark Office